United States Patent [19]

Hou

[11] Patent Number: 4,620,971
[45] Date of Patent: Nov. 4, 1986

[54] INDIUM-BLEOMYCIN COMPLEX

[75] Inventor: De-Yan Hou, Bethesda, Md.

[73] Assignee: The United States of America as represented by the Secretary of the Department of Health and Human Services, Washington, D.C.

[21] Appl. No.: 564,411

[22] Filed: Dec. 22, 1983

[51] Int. Cl.$^4$ .................. A61K 43/00; A61K 49/00
[52] U.S. Cl. .................................... 424/1.1; 424/9
[58] Field of Search ..................... 424/1.1, 9

[56] References Cited

U.S. PATENT DOCUMENTS

| | | | |
|---|---|---|---|
| 3,845,202 | 10/1974 | Tubis et al. | 424/1.1 |
| 3,957,963 | 5/1976 | Sadmon et al. | 424/1.1 |
| 4,017,596 | 4/1977 | Loberg et al. | 424/1.1 |
| 4,057,618 | 11/1977 | Salmon et al. | 424/1.1 |
| 4,311,689 | 1/1982 | Ruddock | 424/1.1 |
| 4,339,426 | 7/1982 | Meares et al. | 424/1.1 |
| 4,360,509 | 11/1982 | Goedemans | 424/1.1 |

OTHER PUBLICATIONS

Schulz et al., Chem. Abstracts, vol. 96 (1982) #30852d.
Blottner et al., Chem. Abstracts, vol. 90, (1979) #2449k.
Van De Poll et al., Chem. Abstracts, vol. 85, (1976) #99182r.
Taylor et al., from *Radiopharmaceuticals*, Eds Subramanian et al., Society of Nuclear Medicine, New York, pp. 458–463, (1975).
Goodwin et al., from Radiopharmaceuticals II, Proceedings 2nd International Symposiom, Seattle, 1979, pp. 275–284.
Orii et al., from *Recent Adv. Nucl. Med.*, 1st Ward Congress of Nucl. Med, Tokyo, 1974, pp. 931–933.

*Primary Examiner*—Christine M. Nucker
*Attorney, Agent, or Firm*—Holman & Stern

[57] ABSTRACT

A new $^{111}$In-BLM complex designated $^{111}$In-BLMC is described. The complex is characterized by a lack of capacity for binding to serum transferrin, a high selective affinity for viable tumor tissue, in vivo stability, improved activity ratios of tumor to tissues over known $^{111}$In-BLM complexes, tumor imaging flexibility and distinctness, and rapid clearance from the body. The new $^{111}$In-BLM Complex thus has clinical use as a radiopharmaceutical for combining radiotherapy and chemotherapy, and as a tumor-imaging agent for diagnosis.

23 Claims, 14 Drawing Figures

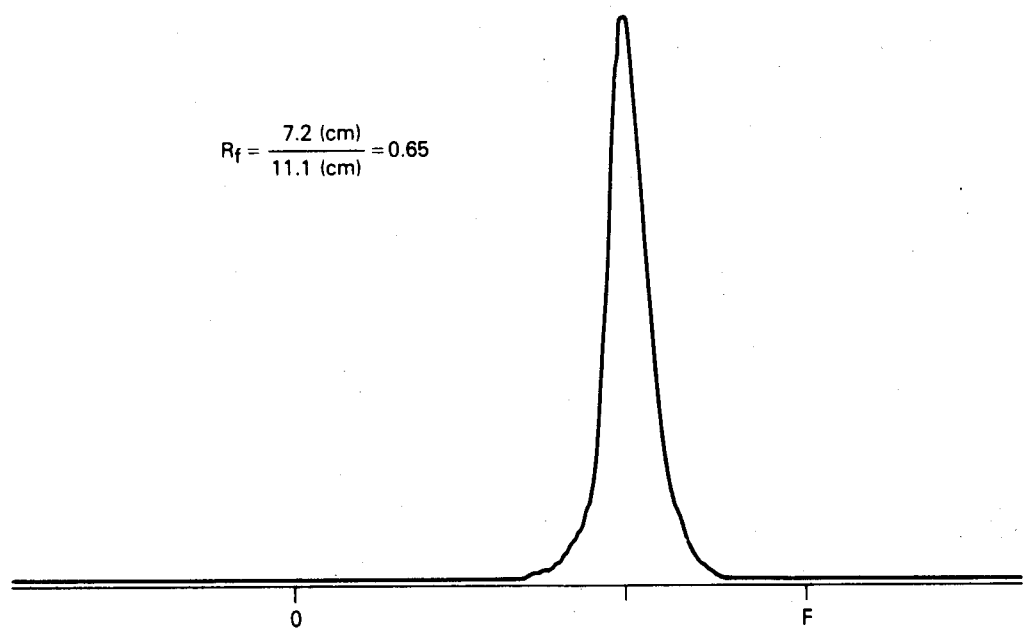
FIG. 2 Radiochromatogram scan of $^{111}$In-BLMC TLC plate
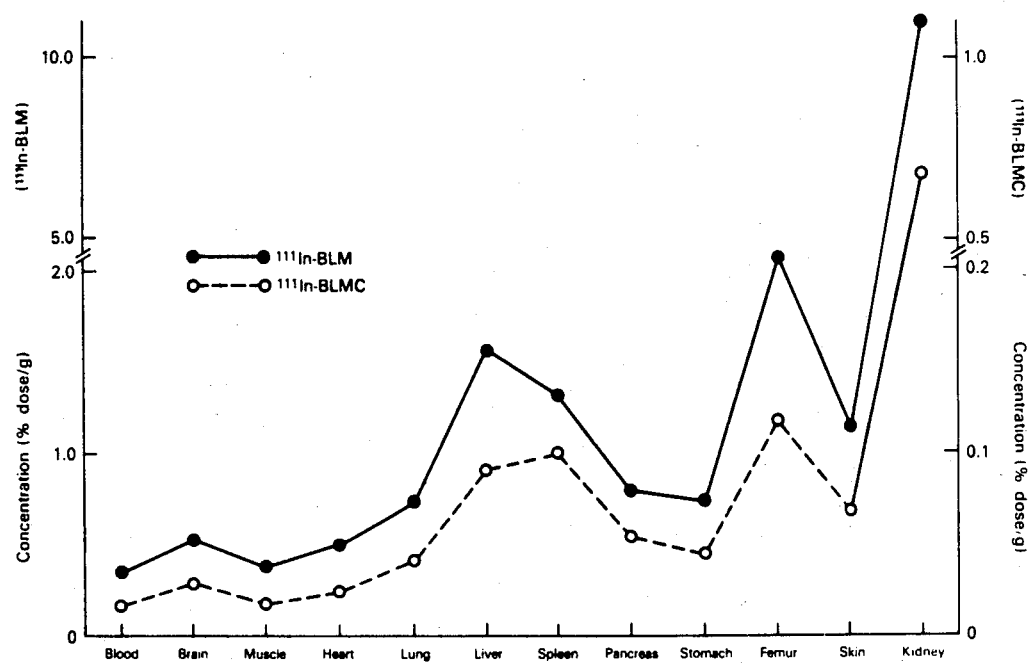
FIG. 6 Tissue concentration of $^{111}$In-BLMC and $^{111}$In-BLM (at 24h)

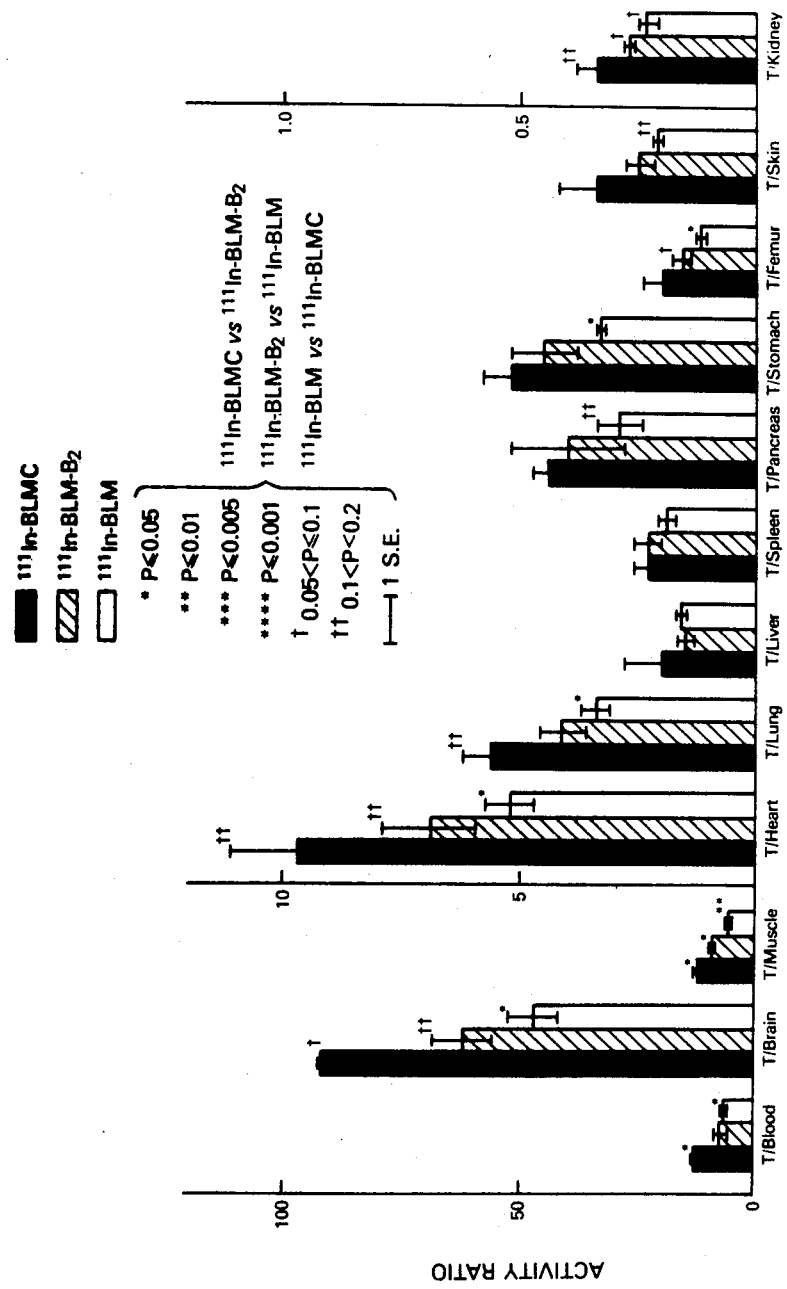
FIG. 7. Activity ratios of tumor to tissue in glioma-bearing mice (at 24 hr)

Percent of retained activity after i.p. injection of radiopharmaceutical

Tumor size and host weight in glioma-bearing mice injected 0.9% NaCl, BLM or $^{111}$In-BLMC (i.p.)

Tumor size and host weight in glioma-bearing mice injected 0.9% NaCl, BLM or $^{111}$In-BLMC (i.t.)

FIG. 13
a)
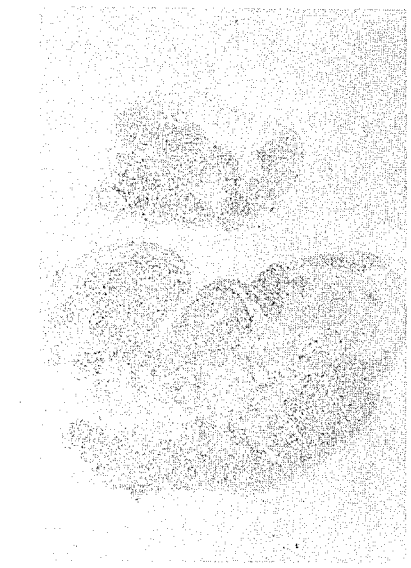
b)
c)
d)
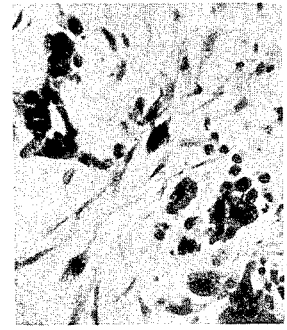
e)
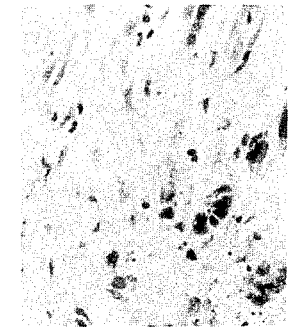

INDIUM-BLEOMYCIN COMPLEX

BACKGROUND OF THE INVENTION

1. Field of the Invention

Bleomycin is a well-known antitumor antibiotic, commercially available as a mixture of bleomycin species differing only in a terminal amine. While particular species such as bleomycin-$A_2$ and bleomycin-$B_2$ have been isolated and characterized, bleomycin is generally employed clinically as a mixture sold under a variety of trademarks such as BLENOXANE (Bristol Laboratories). Bleomycin and its $A_2$ and $B_2$ species are characterized in U.S. Pat. No. 4,339,426, issued July 13, 1982 to Meares, et al.

Bleomycin (BLM) has a selective affinity for a variety of tumors, and exerts its cytotoxic effects on susceptible tumor cells by inducing single-strand breaks in the cell DNA. In addition to its role as a chemotherapeutic, BLM has been chelated with a number of radionuclides for use as a radiopharmaceutical or tumor-imaging agent. These chelates have generally a wider application than BLM alone, as BLM does not exhibit cytoxicity against all tumor tissue to which it has a selective affinity; thus the chelates may function as a radiopharmaceutical, combining both radiotherapy and chemotherapy, or the BLM may merely function as a vehicle for targeting the radionuclide on tumor tissue.

2. Description of the Prior Art

Radiolabelled pharmaceuticals for radio-chemotherapy ideally have a high affinity for tumor tissue, deliver a high dosage of radioactivity to the tumor tissue and a minimal dosage to adjacent tissues, and function to sensitize the tissues to radiation. Complexes of $^{111}$Indium ($^{111}$In) with bleomycin mixtures and bleomycin-$A_2$ or bleomycin-$B_2$ which approach these criteria have been described. These known $^{111}$In-BLM complexes have a high selective affinity for tumor tissue and are relatively safe. $^{111}$In emits both X-radiation and beta radiation, and bleomycin is believed to function as a radiosensitizer. These two properties are important in radiotherapy. $^{111}$In also strongly emits gamma radiation (gamma energies of 173 and 247 kev), and has an effective half-life of 2.8 days; $^{111}$In-BLM complexes are thus potentially useful as tumor-imaging agents. Unfortunately, however, known bleomycin chelates of $^{111}$In bind to serum transferrin. The body is thus broadly exposed to radiation, and the complex is consequently unsuitable for therapy or for use in tumor-imaging. The BLM chelate of $^{57}$Co has been proposed as an alternative to $^{111}$In-BLM; however, the physical half-life of $^{57}$Co (270 days) makes it clinical use as a diagnostic agent impractical.

SUMMARY OF THE INVENTION

The invention comprises a new $^{111}$In-BLM Complex designated $^{111}$In-BLMC. The complex is characterized by a lack of capacity for binding to serum transferrin, a high selective affinity for viable tumor tissue, in vivo stability, improved activity ratios of tumor to tissues over known $^{111}$In-BLM complexes, tumor imaging flexibility and distinctness, and rapid clearance from the body. The new $^{111}$In-BLM Complex thus has clinical use as a radio-pharmaceutical for combining radiotherapy and chemotherapy, and for diagnosis as a tumor-imaging agent.

BRIEF DESCRIPTION OF THE DRAWING

FIG. 2 is a radiochromatograph scan of an $^{111}$In-BLMC TLC plate.

FIG. 6 is a graphical illustration of tissue concentration of $^{111}$In-BLMC and $^{111}$In-BLM, 24 hrs. after administration.

FIG. 7 graphically illustrates activity ratios of tumor to tissue in glioma-bearing mice for $^{111}$In-BLMC, $^{111}$In-BLM-$B_2$ and $^{111}$In-BLM.

FIG. 10a illustrates an autoradiograph of a TLC plate for $^{111}$In-labelled BLM species according to the prior art.

FIG. 10b is an autoradiograph of an electrophoresis plate as a schematically illustrated compilation similar to FIG. 10a.

FIG. 13 is a series of microphotographs comparing tumor size and characteristics after treatment with $^{111}$In-BLM (a) and $^{111}$In-BLMC (b-e).

DETAILED DESCRIPTION OF THE INVENTION

The $^{111}$In-BLMC product of the invention comprises a purified species recovered from an unfractionated BLM mixture labelled with $^{111}$In (III). The product is characterized (FIG. 1a, lane 2) by an Rf of 0.65 (thin layer chromatography on silica plates, employing 10% aqueous ammonium acetate/methanol 1:1, v/v as eluant). Analysis of the thin layer chromatograms by radiochromatograph scanning establishes a radiochemical purity of greater than 99% of the characterized product (FIG. 2). $^{111}$In-BLMC is distinguishable from $^{111}$In-BLM, $^{111}$In-BLM-$A_2$, $^{111}$In-BLM-$B_2$ (—I, —II), and $^{111}$InCl$_3$ by gel electrophoresis (5% agarose, CO$_2$-saturated 0.02M NaHCO$_3$), by migration of $^{111}$In-BLMC toward the anode but a major part of $^{111}$In-BLM, $^{111}$In-BLM-$A_2$ and $^{111}$In-BLM-$B_2$ (-I, -II) toward the cathode, and $^{111}$InCl$_3$ at the origin (FIG. 1b,c). $^{111}$In-BLMC is further distinguishable from known BLM species including $^{111}$In-BLM, $^{111}$In-BLM- A2, $^{111}$In-BLM-B2 (−I, −II), and $^{111}$InCl3, by a lack of binding capacity for serum transferrin.

Figure 1:
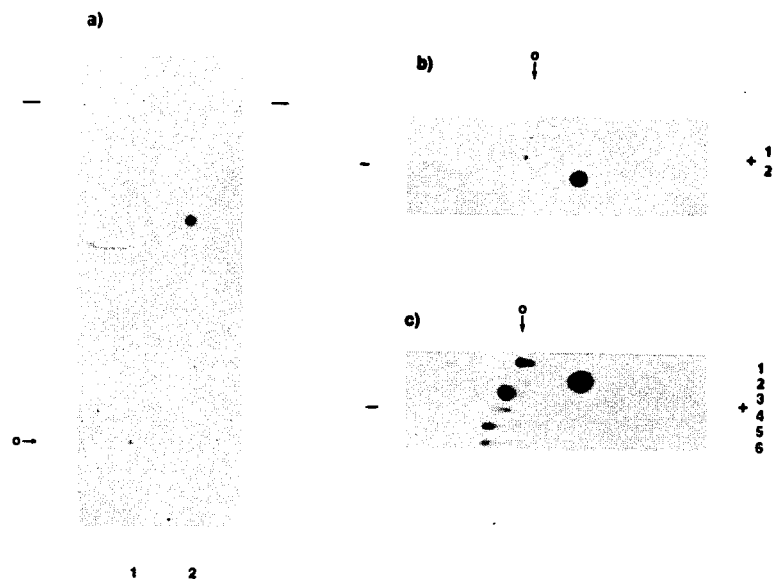
FIG. 1 illustrates autoradiographs of TLC and electrophoresis plates for $^{111}$InCl$_3$ and BLM species labelled with $^{111}$In (III). Lanes 2 are $^{111}$In-BLMC.
Figure 3:
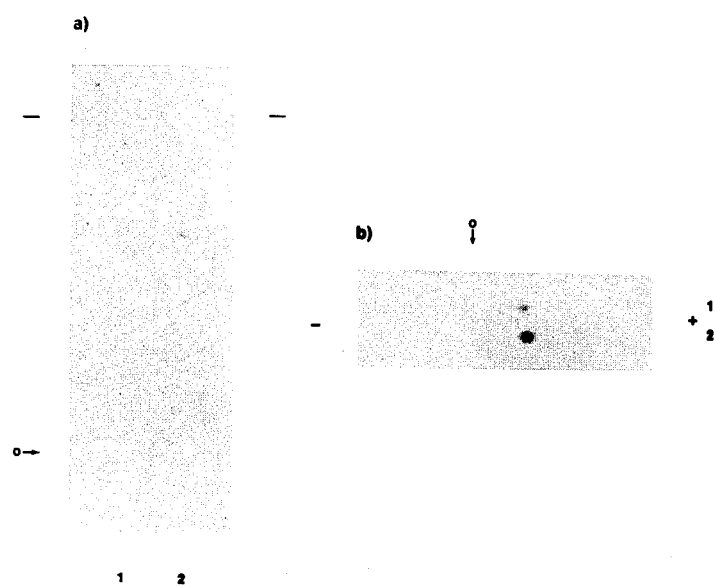
FIG. 3 illustrates autoradiographs of TLC and electrophoresis plates of $^{111}$In-BLMC solutions after storage.

Autoradiographs of TLC and electrophoresis plates for $^{111}$In-BLMC solutions stored at 4° C. for three weeks showed no change in Rf for $^{111}$In-BLMC (FIG. 3a, b:cf. FIG. 1).

The $^{111}$In-BLMC complex of the present invention is stable in vivo: TLC and electrophoresis patterns of urine receiving $^{111}$In-BLMC under in vivo conditions (1-4 or 24 hours after injection) are similar to those of in vitro mixtures of urine with $^{111}$In-BLMC (FIGS. 4(a) and (b), lanes 2 and 4). This is typical of both normal and tumor-bearing mice. Electrophoretic patterns of in vitro mixtures of plasma with $^{111}$In radiopharmaceuticals illustrate that $^{111}$In of $^{111}$InCl3 binds to serum transferrin in vitro, but $^{111}$In-BLM $^{57}$Co-BLM and $^{111}$In-BLMC do not (FIG. 5a—$^{111}$In-BLMC in lane 4; serum transferrin locates near the origin, slightly to anode side, not illustrated). $^{111}$In-BLMC and $^{57}$Co-BLM do not bind to serum transferrin under in vivo conditions in plasma from mice not bearing a tumor, 1-3 hr. after injection (FIG. 5b-In-BLMC in lane 4, serum transferrin located again slightly to anode side of origin, not illustrated.)

The tissue distributions of $^{111}$In-BLMD, $^{111}$In-BLM-B2 and $^{111}$In-BLM in glioma-bearing mice after injection of the pharmaceutical are summarized in Table I. Concentrations in different tissues at 24 hr. are significantly lower for $^{111}$In-BLMC. Activity ratios of tumor to blood and to muscle for $^{111}$In-BLMC are much higher than for $^{111}$In-BLM-B2 and $^{111}$In-BLM (Table II, FIG. 7). Rate of excretion (calculated from percent activity retained in normal mice) for $^{111}$In-BLMC is high (FIG. 8), reflecting the $^{111}$In-BLMC lack of binding capacity for serum transferrin.

PREPARATION AND CHARACTERIZATION OF $^{111}$In-BLMC

Figure 10:
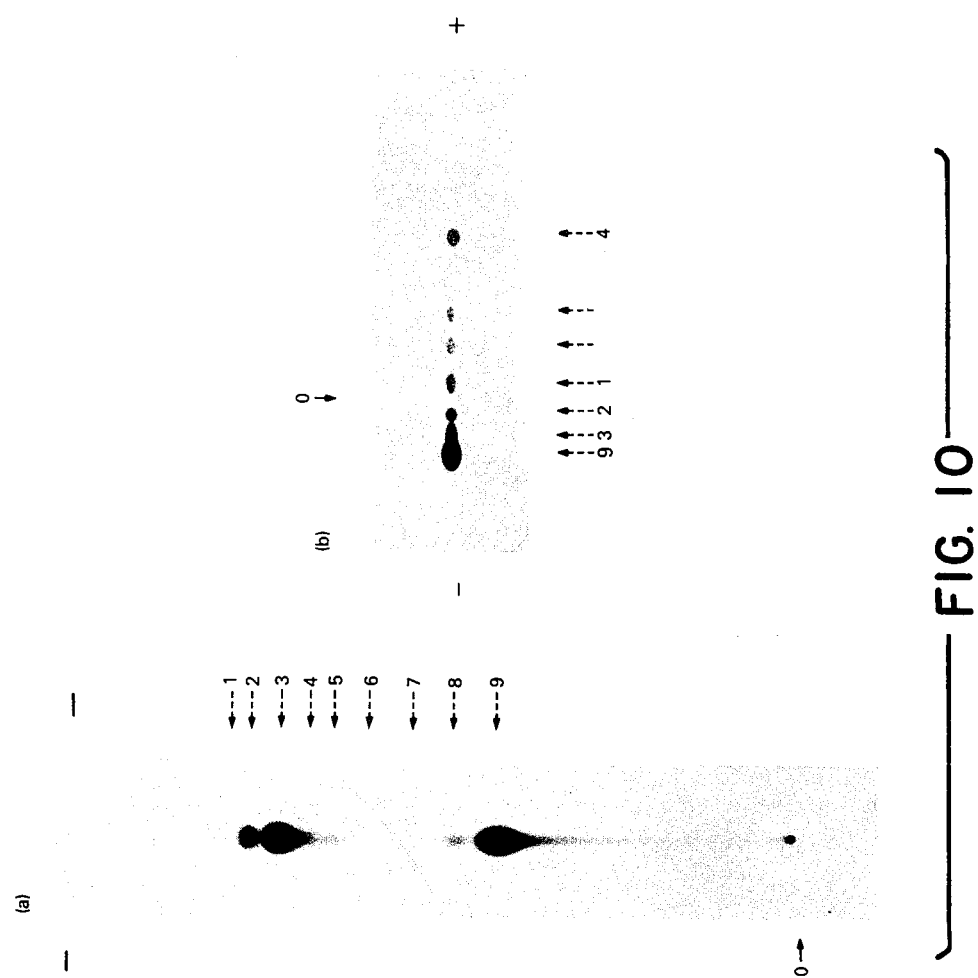

BLM mixture (BLENOXANE) labelled with $^{111}$In by conventional procedures fractionates into several components (FIG. 10). Autoradiographs of TLC plates are shown in FIG. 10a. $^{111}$In-BLM separated into three major components (Rf 0.75, 0.71 and 0.42), and six minor components Rf: 0.78, 0.65, 0.63, 0.59, 0.54, and 0.48).

According to the process of the present invention, a conventional bleomycin mixture is radiolabelled with $^{111}$In(III) at a pH below about 3. The pH of the solution at the time the bleomycin and $^{111}$In (III) are combined appears to be absolutely critical to the production of the $^{111}$In-BLMC species described herein. Under the correct process conditions, the several $^{111}$In-labelled BLM components visible on an autoradiograph of a thin layer chromatogram of conventional labelled BLM (FIG. 10a) are replaced by a single, $^{111}$In-labelled component (Rf 0.65) as illustrated in FIG. 1a. The mechanism of this shift is not known. A possible partial explanation is that the component at Rf 0.65 in lane 4 of FIG. 10a is exclusively labelled with $^{111}$In under the process conditions of the present invention, and is thus the only component visible in the TLC autoradiograph in FIG. 1a. This is, however, merely a postulation at the present time (Example X infra).

Bleomycin mixtures useful as starting materials in the process of the present invention comprise mixtures of glycopeptide antibiotics isolated from the culture broth of *Streptomyces verticillus* by procedures of the type described by Umezawa (*J. Antibiotics* 19A:200, 1962), exemplified by commercial bleomycin mixtures such as BLENOXANE. The bleomycin mixture is radiolabelled with $^{111}$In (III) by combining bleomycin with a suitable solution of $^{111}$In radionuclide, particularly $^{111}$InCl3, commercially obtainable in aqueous HCl at a pH of 1 to 3 (which maintains $^{111}$InCl3 in solution). A diluent is employed, if necessary, so that the $^{111}$InCl3 and BLM react at a pH of below about 3.5, preferably below about 3. At a reaction pH of from about 2 to about 3 (pHydrion paper), a substantially radiochemically pure $^{111}$In-BLMC product is obtained, as illustrated in FIG. 1(a). At a pH lower than about 1.5 and higher than about 3.5, the product will be slightly contaminated with other $^{111}$In-BLM species, it will be progressively further contaminated as the pH decreases or increases in a typical reaction mixture. Since it is contemplated that the $^{111}$InCl3/BLM reaction product of the present invention will be directly usable in clinical applications, for these applications, at lease, it is desirable to obtain a very pure $^{111}$In-BLMC product, and a reaction pH of about 2 to 3 is recommended. In most clinical applications according to the present invention, a slight amount of foreign $^{111}$In-BLM species is not detrimental, and a reaction pH of about 1.5 to 3.5, preferably about 1.5 to 3, is generally acceptable. BLM in either solid or solution form may be combined with $^{111}$InCl3. $^{111}$InCl3 may be combined with BLM in various concentrations; dilute solutions having an $^{111}$InCl3 concentration of about 2mCi/ml and concentrated solutions having an $^{111}$InCl3 concentration of about 5mCi/0.1 ml are commonly commercially available, for example, from Medi-Physics, Emeryville, CA. The proportions of $^{111}$InCl3 to BLM employed are determined by the desired specific activity of the product. It is generally desirable for clinical applications that the BLM be substantially completely labelled, as BLM in large quantities is toxic; an excess of unlabelled BLM, or an excess of unreacted $^{111}$In(III), should be avoided by correct selection of reaction conditions or by subsequent removal of excess reactant, if necessary. A proportion of solid BLM, or its equivalent in solution form, of about 1.0 mg. to about 25 μl to about 200 μl of $^{111}$InCl3 (concentration 2mCi/ml, pH 1-3) will generally be satisfactory, with preferred proportions of 1.0 mg. solid BLM to about 50 μl to 100 μl to $^{111}$InCl3. Under the preferred proportions, combining solid BLM with $^{111}$InCl3 at a concentration of 2mCi/ml, pH 1-3, will generally produce a reaction solution having the requisite pH. The pH of the reaction solution will vary, however, depending upon the pH of the reactants, and the exact amount of reactants employed. If the pH requires adjustment, a diluent is employed which has sufficient alkalinity or acidity to bring the pH of the solutions, as combined, to a pH of below about 3. Satisfactory results have not been obtained by adjustment of pH after the solutions are combined. Suitable diluents for pharmaceutical applications include physiological saline (e.g.,0.9% NaCl, about pH 5.7) to increase the pH, or HCl to lower the pH, or similar pharmaceutically acceptable diluents. The volume of acidifying or alkalinizing diluent required to produce the desired pH in the reaction solution will vary, depending upon the particular diluent employed, the relative alkalinity of the bleomycin mixture, the acidity of the $^{111}$InCl3 solution, and the amounts of both employed. In general, however, for the above-noted proportions of bleomycin to $^{111}$InCl3 (2miCi/ml, pH 1-3), a volume of 0.9% NaCl (about pH 5.7) at least about equal to the volume of $^{111}$InCl$_3$ solution will be required. Generally, a ratio of 0.9% NaCl (about pH 5.7) to $^{111}$InCl$_3$ (2mCi/ml, pH 1-3) of about 1.5:1 to 4:1 v/v will be satisfactory. If concentrated $^{111}$InCl$_3$ is employed (e.g., pH 1-3, 5mCi/0.1 ml, Medi-Physics), a greater volume 0.9% NaCl to $^{111}$InCl$_3$ of about 4:1 to 8:1 v/v) of diluent will usually be required. In the absence of the pH-adjusting diluent, the pH of the reaction mixture is normally from about 4 to about 6, owing to the alkalinity of the bleomycin reactant. Standard methods for preparing $^{111}$In-labelled bleomycin such as by Thakur (*Int. J. Radiat. Isotopes* 24: 357-359, 1973) do not adjust the pH of the reaction solution; the bleomycin is thus typically radiolabelled at a pH of from about 4 to 6, with results as shown in FIG. 10a.

TUMOR IMAGING

Gamma images of glioma-bearing mice show that 4 hours after i.v. injection (FIG. 9a,b) the tumor was more clearly visible with $^{111}$In-BLMC than with $^{111}$In-BLM, and accumulations of activity in liver and background lower for $^{111}$In-BLMC than for $^{67}$Ga-citrate or $^{111}$In-BLM 24 hours after i.p. injection (FIG. 9c-e). $^{67}$Ga-citrate is one of the few tumor-imaging agents presently employed clinically, and its applications are limited; the improved results obtained with $^{111}$In-BLMC, which appears to have no serious disadvantages, will be of great clinical benefit.

COMBINED RADIOTHERAPY AND CHEMOTHERAPY

Figure 11:
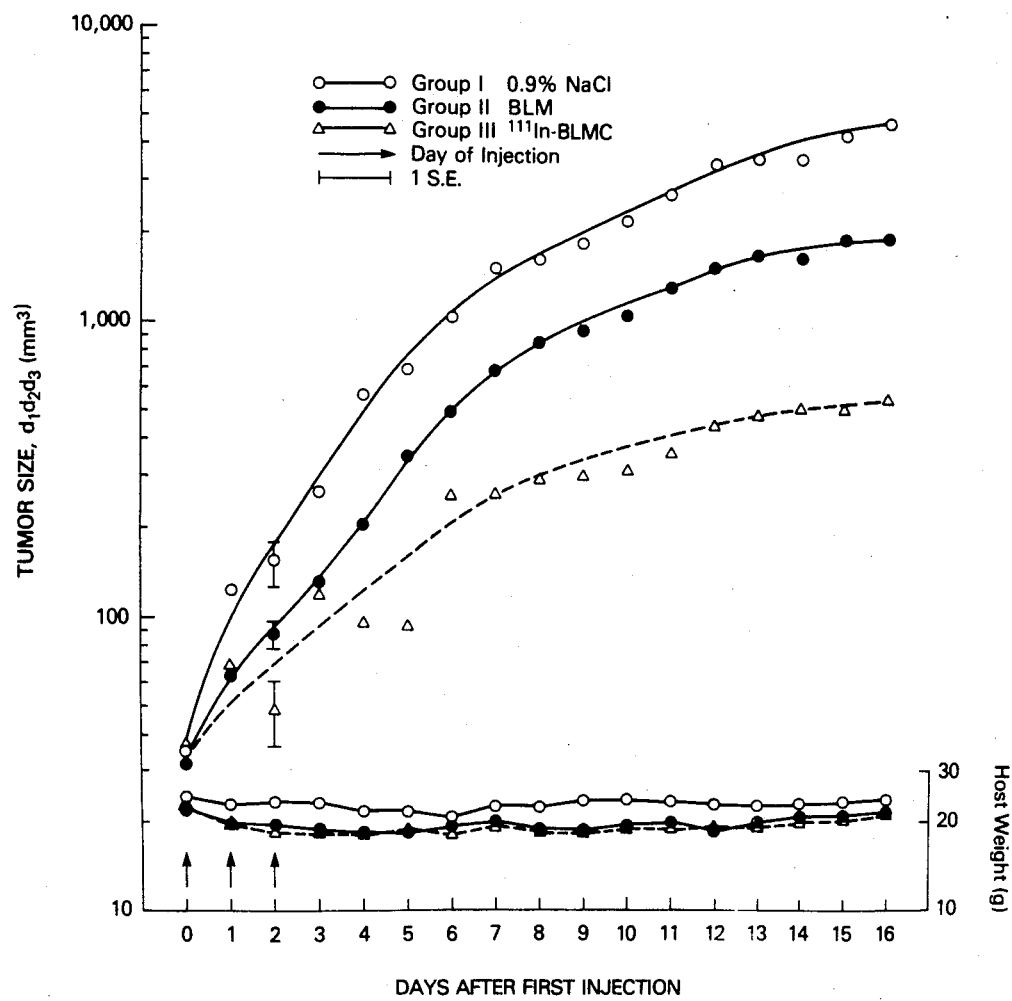
FIG. 11 is a graphic illustration of the effect of 0.9% NaCl, BLM and $^{111}$In-BLMC on tumor size and host weight after intraperitoneal injection.
Figure 12:
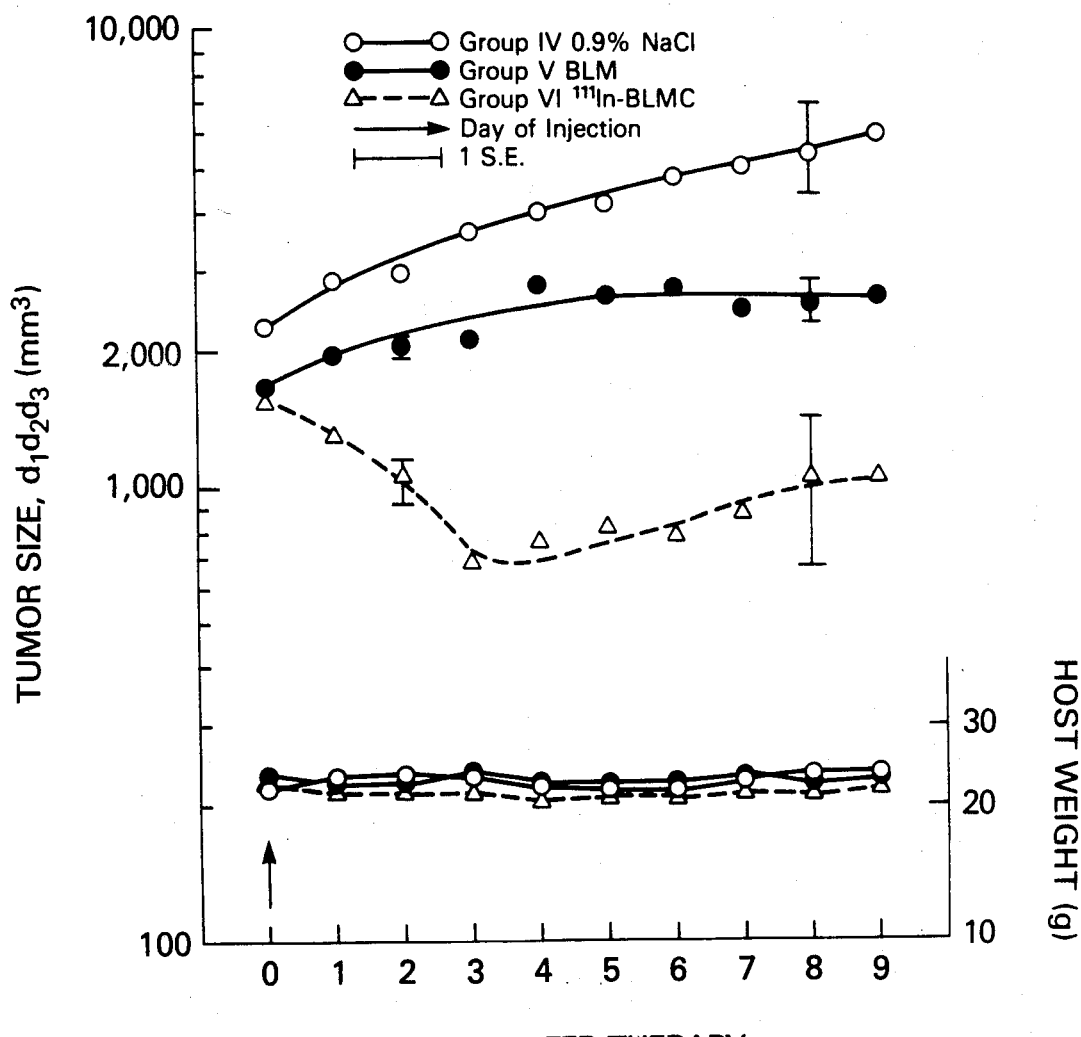
FIG. 12 is a graphic illustration of the effect of 0.9% NaCl, BLM and $^{111}$In-BLMC after into-tumor injection.

Treatment of glioma-bearing mice with $^{111}$In-BLMC by standard protocols produced a significant reduction in tumor size as compared to $^{111}$In-BLM-treated mice. Toxicity of $^{111}$In-BLMC (as reflected in measured host weight) was comparable to that of BLM alone, and only slightly higher than that of the NaCl control group (FIGS. 11 and 12, Tables IV-V). Histopathology of the treated tumors showed that, in comparison to BLM-treated tumors, $^{111}$In-BLMC-treated tumors were smaller and $^{111}$In-BLMC-treated tumors also evidenced newly formed granulation and connective tissue (FIG. 13 c-e).

The use of $^{111}$In-BLMC as a radiopharmaceutical (combined radiotherapeutic and chemotherapeutic) is exemplified herein on glioma-bearing mice, employing standard mouse protocols. Based on these protocols, and standard clinical evaluations (Example IX, infra), $^{111}$In-BLMC is contemplated as an effective tumor-imaging agent and therapeutic drug in the treatment and management of cancer of humans. $^{111}$In-BLMC is particularly contemplated as useful in the treatment and management of gliomas in humans, as these tumors are not particularly sensitive to conventional radiotherapy. $^{111}$In-BLMC of the present invention is also contemplated as applicable, however, to a broad range of tumors in addition to gliomas, such as squamous cell carcinomas and others described in the publication *BLENOXANE (Sterile Bleomyin Sulfate). Clinical Experience Overview*, Bristol-Meyers Company, 1982. As previously noted, bleomycin has a known selective affinity for many tumors. For some, but not all of these tumors, bleomycin is a cytotoxic agent. For others of these tumors, bleomycin may function as a radio-sensitizer, or have no apparent therapeutic value. $^{111}$In-BLMC according to the present invention is potentially useful in the treatment and management of all tumors in humans for which bleomycin has a selective affinity. For susceptible and for metastatic tumors, $^{111}$In-BLMC may produce a combined radiotherapeutic and chemotherapeutic effect, with the bleomycin moiety acting as a cytotoxic agent and/or radiosensitizer, and $^{111}$In as a radio therapeutic. In other tumors, the bleomycin moiety may function solely to deliver $^{111}$In (III) to the target tissue, especially across the tumor cell membrane. In all of these applications, the $^{111}$In-BLMC properties of rapid clearance from the body, stability, low toxicity, and lack of binding to seruum transferrin are especially relevant.

EXAMPLES

MATERIALS AND METHODS

EXAMPLE I

Fractionation of BLM

BLM (BLENOXANE, Bristol Laboratoriess, Syracuse, N.Y.) was separated by thin-layer chromatography (TLC) on silica gel (Analtech). Fifteen units of BLM, dissolved in 15 μl of 0.9% NaCl, was applied in three spots or along one line to the plate, which was developed with 10% ammonium acetate-methanol (1:1 v/v). The positions of BLM fractions were located by ultra-violet light (254 nm). In order to identify the fractions from the relative sizes and positions after chromatography, it was important to apply the samples as spots, the relative amounts of A$_2$ and B$_2$ in the preparation being quoted by the manufacturer. The sections were extracted three times with 0.5% aqueous ammonium acetate-methanol (1:1) and the extracts were taken to dryness with nitrogen.

EXAMPLE II $^{111}$In-labelling of Fractionated BLM and BLM (Prior Art)

The fractions A$_2$ and B$_2$ and unfractionated BLM (Example I) were labeled with $^{111}$In by employing a modification of the method of Thakur (Hou, et al, *Eur. J. Nucl. Med. in press; Int. J. Nucl. Med. & Biol., in press*). $^{111}$InCl$_3$ was received in 0.45% to 0.9% NaCl solution that had been adjusted to a pH of 1-3 with HCl (Medi-Physics). It was taken to complete dryness with nitrogen gas at 55-60 C. BLM or BLM-A$_2$ or -B$_2$ in 0.9% NaCl was added with immediate mixing. The pH of the solutions of $^{111}$In-BLM was between 4.0 and 4.5, and of $^{111}$In-BLM-A$_2$ and -B$_2$ between 5.0 and 5.5 and pHydrion paper (Micro Essential Laboratory Brooklyn, N.Y.). The higher pH for the fractions was caused by the ammonium acetate used for their extraction. The solutions of $^{111}$In-BLM-A$_2$, -B$_2$ and unfractioned $^{111}$In-BLM were tested by TLC. $^{57}$Co-BLM was similarly labelled with the method used for $^{111}$In-BLM.

EXAMPLE III

Labelling Method To Obtain $^{111}$In-BLMC According to Present Invention $^{111}$In-BLMC was prepared by mixing 25-200 μl $^{111}$InCl$_3$, received in 0.45 to 0.9% NaCl solution, adjusted to pH 1-3 with HCl (Medi-Physics), with 1.0 mg of solid BLM or with BLM dissolved in 0.9% NaCl. The final pH of the reaction solution was 2.0-3.0 with pHydrion paper (Micro Essential Laboratory).

In one specific preparation, 3 units solid BLM (BLENOXANE) was dissolved in 1.5-2.5 ml normal saline (0.9% NaCl) solution, about pH 5.7; the BLM solution was then combined with 1.0-1.5 ml $^{111}$InCl$_3$, received in 0.45 to 0.9% NaCl solution, adjusted to pH 1-3 with HCl, at a concentration of 2 mCi/ml. The resulting solution had a pH of between 2 and 3 and contained substantially radiochemically pure $^{111}$In-BLMC; i.e., insignificant amounts of other radio labelled products are present. Solutions produced according to this method are directly usable for tumor imaging or radio- and chemotherapy as described in the following Examples; the proportions of $^{111}$InCl$_3$ employed are adjusted to give a solution of a desired specific activity according to known principles of tumor imaging and radiotherapy.

EXAMPLE IV

TLC and Electrophoresis Procedure

Solutions of $^{111}$In-BLM, $^{111}$In-BLM-B$_2$, $^{111}$-In-BLM-A$_2$, $^{111}$In-BLMC and $^{57}$Co-BLM were analyzed by TLC using 10% ammonium acetate-methanol (1:1 v/v) as the eluant. After applying 0.2 μl of the samples, cold air was blown over the plate for 1–2 minutes. The plate was placed in a TLC cylinder containing freshly prepared eluant and the cylinder immediately covered with a glass plate. All cylinders were enclosed in a sealed plastic bag together with an open beaker containing eluant in order to maintain a saturated atmosphere. One to three, 48-hour urine samples from normal or gliomabearing mice given injections of $^{111}$In-BLM or one of its fractions were also analyzed by this TLC procedure. The same urine samples were also analyzed by gel electrophoresis on 5% agarose (Sigma or BRL low EEO) (Hoch, et al Anal Biochem. 78: 312–317, 1977). The aqueous gel was equilibrated against CO$_2$-saturated 0.02M NaHCO$_3$ and the electrode chambers contained CO$_2$-saturated 0.1M NaHCO$_3$. The run was conducted for about 7 min at 18 V/cm, so that bromphenol blue was displaced 15 mm. In vitro mixtures of 5 parts urine from untreated mice and 1 part of solution of $^{111}$In-BLM or its fraction were similarly analyzed immediately after mixing. The agarose gel plates for plasma samples from normal mice collected 1–3 hr after administration of radiopharmaceutical were dried, autoradiographed, and then stained with Coomassie Blue for protein. The same gel electrophoresis procedure was used for $^{111}$In-BLM, $^{111}$In-BLMC, $^{111}$In-BLM-A$_2$, $^{111}$In-BLM-B$_2$ and $^{57}$Co-BLM; the dried plates were autoradiographed or analyzed with radiochromatogram scanner.

EXAMPLE V

Tissue Distributions and Retention of Radioisotope

Male 6- to 8-week-old C57BL/6 mice received transplants of Glioma-26 in the left leg by a trocar and were given injections with radiopharmaceutical 6 days later. Another group of such mice received $1.5 \times 10^6$ tumor cells in 0.15 ml Hanks balanced salt solution in the left leg and were given injections with radiopharmaceutical 12 days later. $^{111}$In-BLMC, $^{111}$In-BLM-B$_2$, or $^{111}$In-BLM (35 μCi) from Examples II and III were used. The tissue distributions were determined 4 or 24 hr after the mice were given the radiopharmaceutical. The tissues were weighed wet and counted in a scintillation counter.

Figure 8:
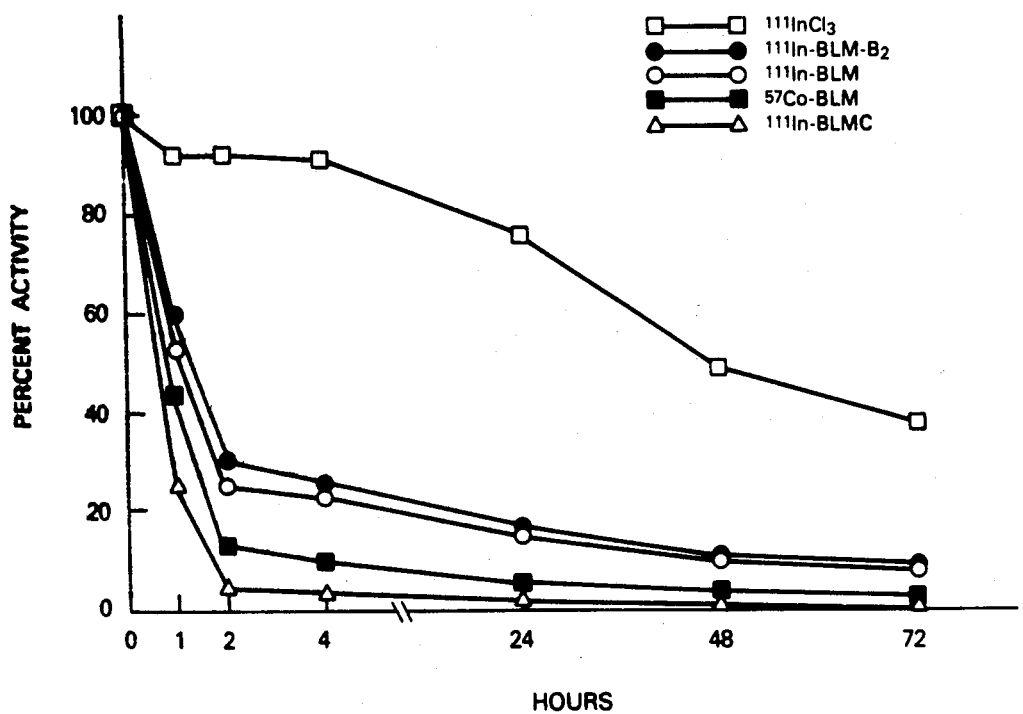
FIG. 8 graphically illustrates percent of retained activity over time (clearance) after administration of $^{111}$InCl$_3$, $^{111}$In-BLM-$B_2$, $^{111}$In-BLM, $^{57}$Co-BLM, and $^{111}$In-BLMC.

Male 6-week-old C57BL/6 untreated, not tumor-bearing, mice were given intraperitoneal (ip) injectons of 30–40 μCi of $^{111}$InCl$_3$, $^{111}$In-BLM-B$_2$, $^{111}$In-BLM, $^{111}$In-BLMC or $^{57}$Co-BLM. At 1, 2, 4, 24, 48, and 72 hr after injection of the radiopharmaceutical, the animal was made to urinate and then the whole body activity was measured in a dose calibrator (FIG. 8).

EXAMPLE VI

Urine and Plasma

The activity distribution in 1–4-hr or 24-hr urine or 1–3-hr plasma from untreated or glioma-bearing mice after injection of radiopharmaceutical was determined by TLC and by gel electrophoresis (Example IV). Mixtures in vitro of urine or plasma from untreated mice with $^{111}$In-BLMC, $^{111}$In-BLM-B$_2$, or $^{111}$In-BLM solution (5:1) (Examples II and III) were also analyzed (Example IV). After autoradiography, dried plasma electrophoresis gels were stained with Coomassie Blue for protein.

EXAMPLE VII

Gamma Images—Tumor Imaging

The 2- to 3-week-old glioma-bearing mice (tumor size: 1.0–1.5 cm) were given injections of $^{111}$In-BLMC, $^{67}$Ga-citrate, or $^{111}$In-BLM into the orbital sinus (or by ip injection). Images were taken with a gamma camera (Raytheon) immediately, 1, 2, 4, 24, and 48 hr after injection by using a pinhole collimator ($\frac{1}{4}$ inch diameter), with the distance of 12 cm between mouse and collimator. $^{111}$In-BLM, and $^{111}$In-BLMC were obtained according to Examples II and III; $^{67}$Ga-citrate was commercially obtained from New England Nuclear (NEN), Boston, Mass.

EXAMPLE VIII

Radiotherapy and Chemotherapy Materials and Methods

Preparation of $^{111}$In-BLMC

Two to 3.2 ml of $^{111}$InCl$_3$ (concentration 2 mCi/ml), received in 0.45 to 0.9% NaCl solution adjusted to pH 1–3 with HCl (Medi-Physics), was mixed with 1.0 mg of solid BLM (Blenoxane, BRISTOL LAB) or with BLM dissolved in 0.9% NaCl. The final pH was 1.5–3.0 by pHydrion paper (Micro Essential Laboratory). As a control, non-radioactive (cold) $^{111}$In-BLMC was prepared similarly with 4-week-old $^{111}$InCl$_3$.

Radiotherapy and Chemotherapy

Glioma 26 transplanted with a trocar in the left hind leg of C57 BL/6 male mice. Six days after transplantation (tumor age: 6 days) the mice were divided into 3 groups, and received intraperitoneal injections (ip groups) daily for 3 days: Group I (n=8)—0.2 ml of 0.9% NaCl; Group II (n=5)—0.004 mg of BLM/g body weight in 0.2 ml of 0.9% NaCl; Group III (n=4)—15 uCi of In-BLMC carried by 0.004 mg BLM/g body weight in 0.2 ml of 0.9% NaCl).

Groups IV-VI received single intratumor injections (it groups) on the 13th day after transplantation: Group IV (n=3)—0.7 ml of 0.9% NaCl/g tumor weight; Group V (n=3—0.5 mg of BLM in 0.7 ml of 0.9% NaCl/g tumor weight; Group VI (n=3)—1.5 mCi of $^{111}$In-BLMC carried by 0.5 mg BLM in 0.7 ml of 0.9% NaCl/g tumor weight.

Two control experiments were made with cold InCl$_3$ (InCl$_3$ that had been stored for 4 weeks and was practically nonradioactive, pH=1–3) and cold In-BLMC (prepared with nonradioactive InCl$_3$ by the same method as that used for $^{111}$In-BLMC, final pH=1.5–3.0). At a tumor age of 6 days, ip injections were given daily for 3 days: Group VII (n=5)—0.2 ml of 0.9% NaCl; Group VIII (n=5)—In-BLMC carried by 0.004 mg BLM/g tumor weight in 0.2 ml of 0.9% NaCl. At a tumor age of 13 days, single doses were given it: Group IX (n=2)—0.7 ml of 0.9% NaCl/g tumor weight; Group X (n=3)—InCl, 0.7 ml/g tumor weight.

The tumor size (product of the three dimensions in $mm^3$) and body weight were measured daily for 16 days following the first injection. Host weight was obtained by subtracting tumor weight from body weight, where tumor weight (g)=tumor size ($d_1 d_2 d_3$, $mm^3$)×0.00053

Histopathology

Several mice were killed on the 22d day after tumor transplantation, and both tumors and tissues were sectioned for histology (H & E stain).

RESULTS

1. TLC and Electrophoresis

TLC autoradiographs of $^{111}InCl_3$ and $^{111}In$-BLMC solutions (FIG. 1a) show $InCl_3$ at the origin and the spot of $^{111}In$-BLMC at Rf 0.65. Electrophoresis autoradiographs of these solutions (FIG. 1b,c) show $^{111}InCl_3$ at the origin, $^{111}In$-BLMC migrating toward the anode (lane 2), and $^{111}In$-BLM-$B_2$(−I, −II), −$A_2$ and most of $^{111}In$-BLM migrating toward the cathode (lanes 3, 4, 5, 6).

Radiochromatogram scans of TLC plates showed the radiochemical purity of $^{111}In$-BLMC to be 99% (FIG. 2).

Autoradiographs of TLC and electrophoresis plates for $^{111}In$-BLMC solutions that had been stored at 4 C. for 3 weeks or more showed no change (FIG. 3a, b).

Autoradiographs of TLC plates of $^{111}In$-BLM labelled according to the prior art and fractionated are shown in FIG. 10a. $^{111}In$-BLM separated into three major components (Rf: 0.75 -lane 2, 0.71 -lane 3, designated B −I, $B_2$, −II) and 0.42 -lane 9, ($A_2$)) and six minor components (Rf: 0.78, 0.65, 0.63, 0.59, 0.54 and 0.48). The latter appeared in autoradiography on longer exposure. Autoradiographs of $^{111}In$-BLM after electrophoresis (FIG. 10(b), a composite diagram from $^{111}In$ tagged fractions and many electrophoresis autoradiographs) show on the cathodic of the origin two major components, $^{111}In$-BLM-$A_2$ (lane 9) and $B_2$-II (lane 3), and near the origin 1 major component, $B_2$-I (lane 2). On the anodic side four minor components were seen. The electrophoretic patterns of $^{111}InCl_3$, $^{111}In$-BLMC and of the separated fractions $^{111}In$-BLM-$B_2$-I, -$B_2$-II, $A_2$ are shown in FIG. 1(b,c).

2. Urine and Plasma

Figure 4:
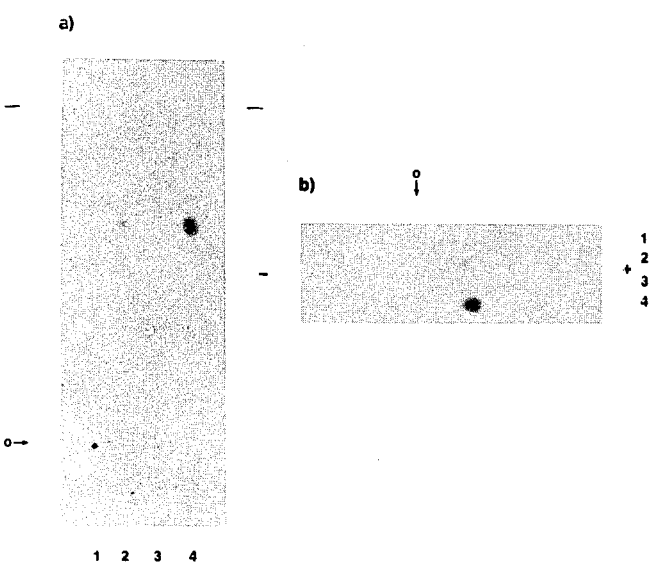
FIG. 4 illustrates autoradiographs of TLC and electrophoresis plates of in vitro mixtures of urine with $^{111}$In-BLMC and $^{111}$InCl$_3$.

TLC and electrophoresis patterns of urine receiving $^{111}In$-BLMC under in vivo conditions (1–4 or 24 hr after injection) were similar to those of in vitro mixtures of urine with $^{111}In$-BLMC, but differed from the patterns for $^{111}InCl_3$ (FIGS. 4a,b). This was the case for both untreated and tumor-bearing mice ($^{111}In$-BLMC, lanes 2 and 4).

Figure 5:
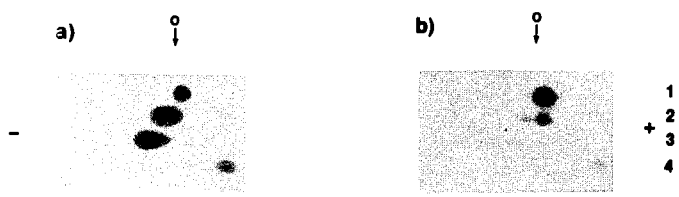
FIG. 5 illustrates autoradiographs of electrophoresis plates of in vitro and in vivo mixtures of plasma with $^{111}$In-BLMC, $^{57}$Co-BLM, $^{111}$In-BLM, and $^{111}$InCl$_3$.

Electrophoretic patterns of in vitro mixtures of plasma with radiopharmaceutical solution show that $^{111}In$ of $^{111}InCl_3$ binds to transferrin (land 1), but $^{111}In$-BLM, $^{57}Co$-BLM and $^{111}In$-BLMC do not (lanes 2–4) (FIG. 5a). Similarly, no binding to transferrin occurred under in vivo conditions in plasma from mice not bearing a tumor, 1–3 hr after injection of $^{111}In$-BLMC (lane 4) or $^{57}Co$-BLM (lane 3) (FIG. 5b).

3. Tissue Distribution and Retention of Radioisotope

The distributions of $^{111}In$-BLMC, $^{111}In$-BLM-$B_2$ and $^{111}In$-BLM among tissues of glioma-bearing mice 4 hr and 24 hr after injection of the radiopharmaceutical are shown in Table I. At 24 hr, the concentrations (% dose/g) in tumor, lung, liver, stomach, and kidney were significantly lower for $^{111}In$-BLMC than for $^{111}In$-BLM, which, in turn, were lower than those for $^{111}In$-BLM-$B_2$. FIG. 6 shows that the concentrations (% dose/g) in different tissues of $^{111}In$-BLMC run almost parallel to those of $^{111}In$-BLM.

The activity ratios of tumor of tissue (Table II, FIG. 7) show that the activity ratios of tumor to blood and to muscle for $^{111}In$-BLMC of 13.1 and 12.4 were significantly higher than those for $^{111}In$-BLM-$B_2$ (7.1 and 9.1) or $^{111}$-In-BLM (6.6 and 6.3) at 24 hr after injection of the radiopharmaceutical. Ratios of tumor to brain, heart, lung, stomach and femur were also significantly higher for $^{111}In$-BLMC than for $^{111}$-In-BLM.

At 4 hr after ip injection (n=3), the activity ratio of tumor to blood was 5.0 fo $^{111}In$-BLMC, which was significantly ($P<0.005$) higher than 1.5 for $^{111}In$-BLM (Table II). Table III shows that the activity ratios of tumor to blood and brain for ip $^{111}In$-BLMC were significantly about twice as high at 24 hr than at 4 hr, while the ratios of tumor to muscle, lung and stomach were slightly, but not significantly, higher.

The percent activity retained in normal mice (n=2) after injection of the radiopharmaceutical (FIG. 8) shows that the rate of excretion increased in the following order, reflecting descreasing binding capacity for transferrin: $^{111}InCl_3$, $^{111}In$-BLM-$B_2$, $^{111}In$-BLM, $^{57}Co$-BLM, $^{111}In$-BLMC.

4. Gamma Images

Figure 9:
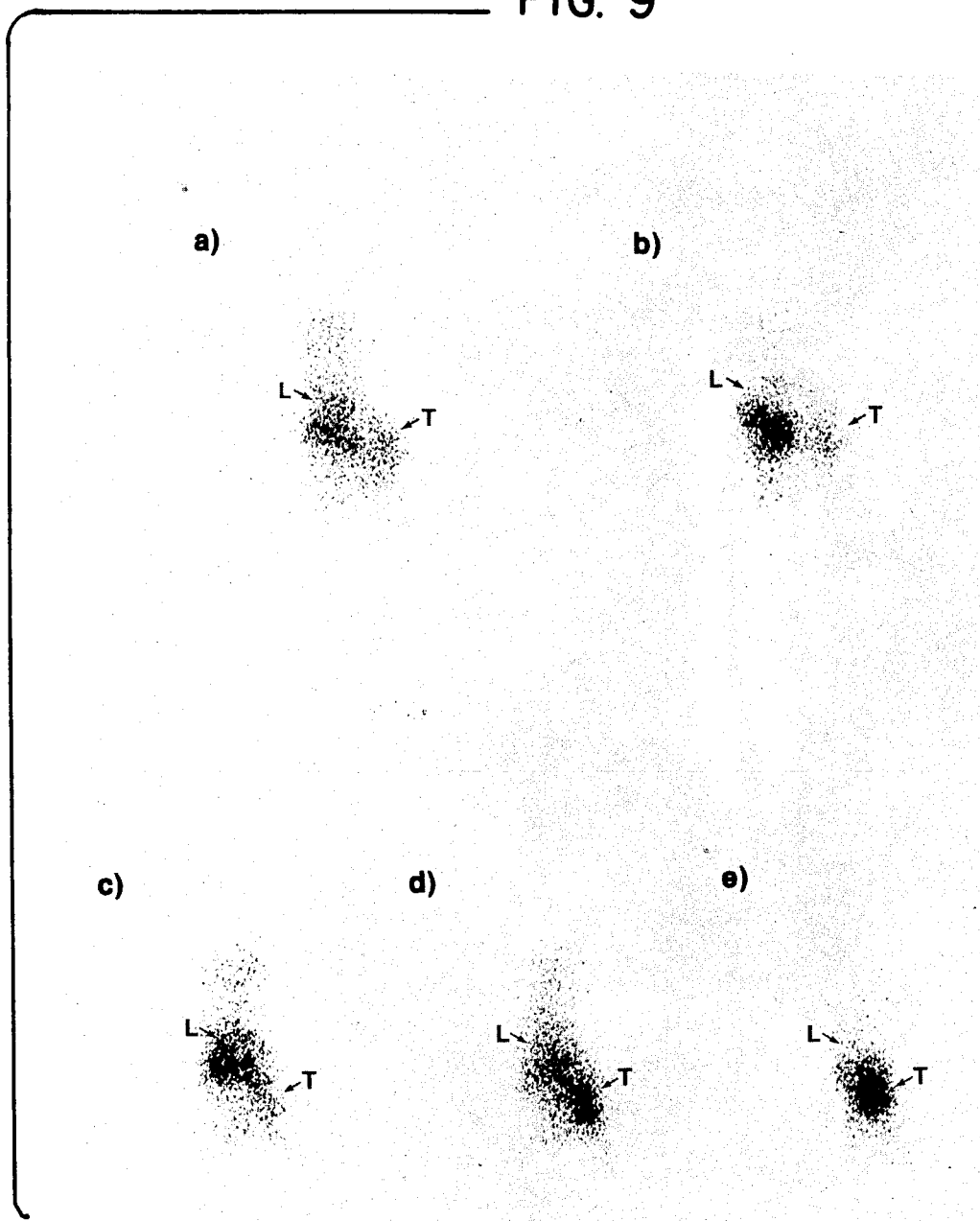
FIG. 9 is a series of gamma camera photographs of tumor accumulation of radioactivity for $^{111}$In-BLMC, $^{67}$Ga-citrate, and $^{111}$In-BLM, 4 hr. or 24 hr. after injection.

Gamma images of glioma-bearing mice given injections of $^{111}$-In-BLMC, $^{67}Ga$-citrate or $^{111}In$-BLM (FIG. 9) show that 4 hr after injection (FIG. 9a,b) the tumor was more clearly visible with $^{111}In$-BLMC (FIG. 9b) than with $^{111}In$-BLM (FIG. 9a), and the accumulations of activity in liver and background were lower for $^{111}In$-BLMC than those for $^{111}In$-BLM. FIG. 9 c–e shows that 24 hr after i.p. injection the accumulation of radioactivity in the tumor was higher for $^{111}In$-BLMC (FIG. 9e) than that for $^{67}Ga$-citrate (FIG. 9d), or $^{111}In$-BLM (FIG. 9c), and the activity of liver and background were lower for $^{111}In$-BLMC than those for $^{67}Ga$-citrate or $^{111}In$-BLM. The $^{111}In$-BLMC according to the invention is useful in known tumor imaging processes, such as those described in U.S. Pat. No. 4,339,426, (supra), U.S. Pat. No. 4,057,618 issued Nov. 8, 1977 to Salmon, et al, U.S. Pat. No. 4,311,689, issued Jan. 19, 1982 to Ruddock; U.S. Pat. No. 3,845,202 issued Oct. 29, 1974 to Tubis, et al, U.S. Pat. No. 4,360,509 issued Nov. 23, 1982, to Goedemans; and U.S. Pat. No. 4,017,596, issued Apr. 12, 1977 to Loberg, et al; each of these patents is incorporated herein by reference.

5. Radiotherapy and Chemotherapy

Tumor size and host weight in glioma-bearing mice after ip therapy are shown in TABLE IV and FIG. 11. During the observation interval, the tumor size in the $^{111}In$-BLMC Group (III) was smaller by a factor of 1.8–3.8 when compared to that in the BLM Group (II) ($p<0.05$ or $p<0.001$ until day 16) which, in turn, were smaller by a factor of 1.8–2.8 than that in the NaCl Group (I) ($p<0.05$ or $p<0.001$ until day 12 after the first injection). The tumor size in the $^{111}In$-BLMC-treated group was smaller by a factor of 3.2–8.6 when compared to that in the NaCl Group. At day 16 after the first injection, the tumor size in the $^{111}In$-BLMC group was 560 (range 240–1030)$mm^3$, which was smaller than 1980 (range 1400–3290)$mm^3$ in the BLM Group, $p<0.025$; the tumor size in the BLM group was smaller than that in the NaCl Group 4830 (range 2580–9180)mm ($0.1<p<0.2$). During days 1 to 12 after the first injection, the host weight in the BLM Group was approximately 20% less than that in the NaCl Group. Toward the final days the difference in host weight was only about 10%. Host weights in the $^{111}$In-BLMC and BLM groups were similar, and recovered to almost the original values.

TABLE V and FIG. 12 show the therapeutic effect of $^{111}$In-BLMC in the it group. The tumor size for the $^{111}$In-BLMC Group (IV) decreased steadily for 3 days, then remained significantly smaller than that in the BLM Group (V) until the 9th day of therapy. On the 9th day of the experiment, the tumor size in the $^{111}$In-BLMC Group was 1060 (range 680–1810)mm$^3$, which was smaller than 2680 (range 2060–3210)mm$^3$ seen in the BLM Group (p<0.05), and the latter was smaller than 6020 (range 4060–7070)mm$^3$ in the NaCl Group (p<0.05). The differences in the host weights for these groups were not significant.

Tumor size and host weight for the two experiments with cold InCl$_3$ and In-BLMC are shown in TABLES VI and VII. In the ip groups, during days 4 to 16 after the first injection, the tumor size was significantly smaller by a factor of 1.6–2.6 for cold In-BLMC (Group VIII) than for NaCl (Group VII, except for day 9 after the first injection, for which p=0.1). During days 2–4 the hose weight in the In-BLMC group was 10% less than that in the NaCl group. In the it groups for cold InCl$_3$ (Group X) and NaCl (Group IX), the tumor sizes increased and were similar.

6. Histopathology

FIG. 13 a,b shows that the tumor size for the $^{111}$In-BLMC group was smaller than that for the BLM group, and that more necrotic tissue was present in tumors of the $^{111}$In-BLMC (ip) group than in those of the BLM (ip) group. FIG. 13c–e shows newly-formed granulation and connective tissue in the tumor of the ip and it $^{111}$In-BLMC groups, indicating replacement of tumor cells.

Liver and kidney morphology (not illustrated) were similar for the $^{111}$In-BLMC, BLM, and 0.9% NaCl groups (both ip and it). Abnormalities were not found in these groups.

EFFICACY AND TOXICITY

The results indicate that $^{111}$In-BLMC is more effective than BLM alone in the treatment of glioma-bearing mice. $^{111}$In-BLMC appears preferable to BLM alone because: (1) it reduced the tumor size in the ip group to one-ninth of that for the NaCl group and in the it group to one-sixth of that for the NaCl group, while for BLM alone the figures were one-third and one-half; and (2) the necrotic area was increased to a greater extent by $^{111}$In-BLMC than by BLM. To study the toxicity of $^{111}$In-BLMC, the morphology of kidney and liver (which received the highest radiation dose) was investigated, and no differences were found among the $^{111}$In-BLMC, BLM and NaCl Groups. The host weight in the $^{111}$In-BLMC and BLM groups did not differ. The host weights for BLM (Group II) was 20% less than that for NaCl (Group I), but for In-BLMC (Group VIII) it was only 10% less than for NaCl (Group VII). The host weights had recovered in 15 days for BLM and recovery was complete in 3 days for In-BLMC. The quicker return of hose weights suggest less toxicity for cold In-BLMC than for BLM.

Human glioma, especially Grade II and IV astrocytoma, is not particularly sensitive to radiotherapy. The mechanism of the effects of $^{111}$In-BLMC on experimental gliomas is not known. In these experiments, the tumor sizes remained similar for cold InCl$_3$ (Group X) and for NaCl (Group IX, TABLE VII), i.e., cold InCl$_3$ did not affect glioma. For cold In-BLMC (Group VIII), the tumor size became smaller than that for NaCl (Group VII) by a factor of 1.6–2.6 (Table VI), and for BLM (group II) it became similarly smaller than that for NaCl (Group I) by a factor of 1.8–2.8 (Table IV). For radioactive $^{111}$In-BLMC (Group III), the tumor size became smaller than that for NaCl (Group I) by a factor of 3.2–8.6 (Table IV). Thus, radioactive $^{111}$In did play a major role in the effectiveness of $^{111}$In-BLMC against glioma. Moreover, in our experiments, the absorbed dose of the tumor in the ip group of $^{111}$In-BLMC was about 60 rad, and this dose is not large enough for radiotherapy alone.

It has been reported that BLM has special affinity for ectodermal tissue and gliomas are of ectodermal origin. BLM also inhibits the growth of cultured human glioma cells. BLM is further known to be effective against squamous cell carcinomas, malignant lymphomas, testicular, cervical, and lung neoplasms, and head and neck cancers. It is believed that $^{111}$In-BLMC will have a therapeutic effect on all known tumors susceptible to the pharmaceutical effects of BLM, or for which BLM has a selective affinity.

CLINICAL

It is of interest to compare the ratios of tumor does to whole body dose received when treating with $^{111}$In-BLMC and the previously studied $^{111}$In-BLM. Present data have shown that the concentrations (%dose/g) of $^{111}$In-BLMC and $^{111}$In-BLM in 12 different tissues vary almost in parallel (FIG. 6). The time integral of the whole body activity was 5.8 times as high for $^{111}$In-BLM as that for $^{111}$In-BLMC. The whole body dose then can be estimated to be 5.8 times as large for $^{111}$In-BLM when compared with $^{111}$In-BLMC.

In the described experiments, the mice were given 15 mCi of $^{111}$In-BLMC carried by 4 mg of BLM/kg body weight. The standard BLM dosage in the human is 0.25–0.5 mg/kg; this is smaller by a factor of 8–16 when compared to the doses used to treat the mice (4 mg BLM/kg). Therefore, it is proposed that one tenth of this dose may be effective for patients, i.e., 1.5 mCi of $^{111}$In-BLMC carried by 0.4 mg of BLM/kg body weight. The radiation dose of kidney, liver and red bone marrow was 1.64, 1.61 and 0.797 rad/mCi, respectively, for $^{111}$In-BLM administered to patients. Therefore, it is estimated that the dose should be about 0.28, 0.28 and 0.14 rad/mCi for $^{111}$In-BLMC. From the ratios of tumor to liver (1.9) and to blood (13.1) for $^{111}$In-BLMC, the dose to tumor was estimated to be about 60 rad for a 60-kg patient who would receive 1.5 mCi of $^{111}$In-BLMC/kg body weight. It has been reported that doses of 3000 to 3500 rads for liver and 2000 rads for kidney, delivered over a 3- to 4-week period, and less than 200 rads to bond marrow are safe. Thus, if fractionated, 60–90 mCi (1.5 mCi/kg) of $^{111}$In-BLMC per dose would deliver a presumably safe dose of 15 times within a 3- to 4-week period; for a larger dose, given fewer times, the radiation would be even safer. A standard clinical protocol for clinical evaluation of $^{111}$In-BLMC is annexed hereto as Example IX.

EXAMPLE IX

Clinical Evaluation of A New Tumor Imaging agent-$^{111}$In-Bleomycin Complex (Protocol)
1. We have discovered a new $^{111}$In-Bleomycin Complex (BLMC), which has high affinity to tumor, does not bind to transferrin and is stable in vivo. In tumor-bearing mice and rats, tumors were imaged more distinctly with the new $^{111}$In-BLMC and $^{57}$Co-BLM than with $^{67}$Ga-citrate. The tissue distribution shows that $^{111}$In-BLMC can substitute for $^{57}$Co-BLM and is much superior than $^{67}$Ga-citrate; it was effective for combining radiotherapy and chemotherapy in glioma-bearing mice.

2. Animal Toxicity Studies:
Lewis rats, female, 160–170 g,

TABLE A

| | | Parameters for Dosimetry calculations | | | | |
|---|---|---|---|---|---|---|
| | Initial | Biological $T_b \frac{1}{2}$ | | Dose | | |
| Time | (% dose/g) | Curve 1 (0–4 h) | Curve 2 (4 h) | (RAD) | Dose/mCi | Dose × 10 (rads)*** |
| Total* | 100 | 0.5 | 24 | 0.03 | 0.003 | 0.3 |
| Blood | 10 | 0.3 | 14.4 | 0.02 | 0.002 | 0.2 |
| Liver | 1.7 | 0.6 | 20 | 0.02 | 0.002 | 0.2 |
| Kidney | 13 | 0.7 | 13.6 | 0.12 | 0.012 | 1.2 |
| Femur | 7.5 | 0.5 | 16.6 | 0.03 | 0.003 | 0.3 |
| Testicle | 1.1 | 0.6 | 30 | 0.01 | 0.001 | 0.1 |
| Urine | 54 | 1.6 | 9.5 | 0.77 | 0.077 | |
| Urinary Bladder Wall | | | | <0.39** | 0.04 | <3.9 |

*Data from normal mice.
**From dose of urine divided by 2, because radiation is not isotropic
***Safety factor control group: i.p. 0.5 ml of 0.9% NaCl, n=4
test group: i.p. 2 mCi of $^{111}$In-BLMC carried by 5 mg BLM/kg in 0.5 ml 0.9% NaCl, n=3. This is equal to 10 times the planned human dose.*
*the minimally active dose is 2 unit of BLM, the regular dose of BLM for a patient is 0.25–0.5 unit/kg, and the dose BLM as carried for $^{111}$In-BLM or $^{57}$Co-BLM in clinical diagnosis is 5–15 units.

The rats were killed 2 weeks after administration of $^{111}$In-BLMC and the organs were sectioned for histology. The morphology of liver, kidney, ovary, heart, lung, stomach, spleen, pancreas and femur were similar for the $^{111}$In-BLMC and 0.9% NaCl groups. Abnormalities were not found in these groups.

3. Studies on large animals for imaging:
One dog bearing venereal tumor, which was innoculated 1 year earlier, was given an i.v. injection of $^{111}$In-BLMC 200 μCi carried by 0.1 unit BLM/Kg body weight, (the dose was 5 mCi $^{111}$In-BLMC carried by 3 unit BLM). The dog was imaged 24 and 48 hours later. In this observation period, all of the dog's three tumors showed activity uptake. Kidney and bladder had more intense activity than the tumors. At 48 hours, the background was less intense than at 24 hours.

4. Patient Selection
Scintigraphic localization of lung cancer in a group of 5 patients. A comparison of $^{111}$In-BLMC with $^{57}$Co-BLM.

5. Method of labelling (for human use)
5–10 mCi $^{111}$InCl$_3$ (received in 0.1–0.2 ml of 0.45% to 0.9% NaCl solution, adjusted to pH 1–3 with HCl) was mixed with 3 unit of BLM* (Bristol Lab) dissolved in 0.8 ml of 0.9% NaCl. The final pH was 2.0 to 3.0 with pHydrion paper (Micro Essential Lab). This solution was prepared sterile.

6. Method of Imaging:
Gamma camera images are obtained at 1,2,4,24,48 hours after injection. Data will be stored on computer for later analysis.

7. Toxicity:
BLM is contraindicated in patients who have demonstrated a hypersensitive or an idiosyncratic reaction to it.

8. Radiation Dosimetry
Tissue distribution (% dose/g) of $^{111}$In-BLMC were calculated from the data for glioma-bearing mice (6 days after tumor transplantation), 1, 2, 4, 8 or 24 h after ip injection. Initial concentration were obtained by extrapolation to zero. The dose was calculated from the injected dose of 200 μCi $^{111}$In/kg (12 mCi administered to a 60 ky patient, 4 μCi/20 g for mice). Table A shows the parameters used for calculation.

The absorbed dose for 1 mCi $^{57}$Co-bleomycin is 0.4 rad for liver, 2.0 rad for kidney and 1.4 rad for bladder. The total dose of 12 mCi $^{111}$In-BLMC and 1 mCi $^{57}$Co-BLM for one patient would be 0.42 rad for liver, 2.12 rad for kidney and 1.79 rad for bladder.

TABLE B

| Dose Calculation for $^{111}$In—BLMC | | |
|---|---|---|
| Radiation Type | Energy (keV) | (g-rad/μCi-h) |
| $^{111}$In EC Decay (2.83 d l) | | I (min) = 0.10% |
| Auger-L | 2.72 | 0.0058 |
| Auger-K | 19.3 | 0.0065 |
| Ce—K— 2 | 144.57 3 | 0.0259 |
| Ce—L 2 | 167.26 3 | 0.0037 |
| Ce—M NO— 2 | 170.51 3 | 0.0009 |
| Ce—K— 3 | 218.679 20 | 0.0235 |
| Ce—L— 3 | 241.372 20 | 0.0040 |
| Ce—NMO— 3 | 244.620 20 | 0.0009 |
| X-ray L | 3.13 | 0.0005 |
| X-ray K$_{\alpha 2}$ | 22.98410 2 | 0.0116 |
| X-ray K$_{\alpha 1}$ | 23.17360 2 | 0.0220 |
| X-ray K$_\beta$ | 26 | 0.0081 |
| 2 | 171.28 3 | 0.329 |
| 3 | 245.390 20 | 0.491 |

Δ(g.rad/μci.h) of $^{111}$In: electron group 0.0712,
low energy photon part: 0.0422 × 0.05 = 0.0021
higher energy photon part: 0.820 × 0.01 = 0.0082
total Δ(ΣΔ) = 0.0815 g.rad/μci.h <Blood>
(1) 0–4h:
Dose rate: 0.0815 (g.rad/μci.h) × 10% (% dose/g) × 4(μCi) = 0.033 rad/h Dose: $0.033 \times \int_0^4 e - \frac{0.693}{T} dt = 0.033 \times$
$\frac{0.3}{0.693} (e - \frac{0.6934}{0.3} - e - \frac{0.0693}{0.3}) \times$
$= 0.014 \times (0.0000971 - 1) = 0.014$ rad (2) 4–∞h:

TABLE B-continued

Dose Calculation for $^{111}$In—BLMC

Dose rate:    $0.0815 \times 0.04\% \times 4 = 0.0001$

Dose:    $0.0001 \times \dfrac{14.4}{\ln 2} = 0.002$

<liver>

(1) 0–4h:

Dose rate:    $0.0815 \times 1.7\% \times 4 = 0.006$ rad/h

Dose:    $0.006 \int_0^4 e - \dfrac{0.693t}{T} dt = -0.006 \times \dfrac{0.6}{0.693} (0.0098528 - 1) = 0.005$ rad (2) 4–∞h Dose rate:    $0.0815 \times 0.12\% \times 4 = 0.0004$ Dose:    $0.0004 \times \dfrac{20}{0.693} = 0.012$ (1) + (2):    0.02 rad <kidney>

(1) 0–4h:

Dose rate:    $0.0815 \times 13\% \times 4 = 0.042$

Dose:    $0.042 \int_0^4 e - \dfrac{0.693t}{T} dt = -0.042 \times \dfrac{0.7}{0.693} (0.0190631 - 1) = 0.042$ (2) 4–∞h:

Dose rate:    $0.0815 \times 1.3\% \times 4 = 0.004$

Dose:    $0.004 \times \dfrac{13.6}{0.693} = 0.079$ (1) + (2):    0.12 rad

<femur>

(1) 0–4h

Dose rate:    $0.0815 \times 7.5\% \times 4 = 0.025$ rad/h

Dose:    $0.025 \int_0^4 e - \dfrac{0.693t}{T} dt = -0.025 \times \dfrac{0.5}{0.693} (0.0039109 - 1) = 0.018$ rad (2) 4–∞h Dose rate:    $0.0815 \times 0.16\% \times 4 = 0.0005$ rad/h Dose:    $0.0005 \times \dfrac{16.6}{0.693} = 0.012$ rad (1) + (2):    0.03 rad <testicle>

(1) 0–4h:

Dose rate:    $0.0815 \times 1.1\% \times 4 = 0.004$ rad/h

Dose:    $0.004 \int_0^4 e - \dfrac{0.693t}{T} dt = -0.004 \times \dfrac{0.6}{0.693} (0.0098528 - 1) = 0.003$ (2) 4–∞h:

Dose rate:    $0.0815 \times 0.05\% \times 4 = 0.0002$ rad/h

Dose:    $0.0002 \times \dfrac{30}{0.693} = 0.009$ rad (1) + (2):    0.01 rad

<urine>

(1) 0–4h

Dose rate:    $0.0815 \times 54\% \times 4 = 0.18$ rad/h

Dose:    $0.18 \int_0^4 e - \dfrac{0.693t}{T} dt = -0.18 \times \dfrac{1.6}{0.693} (0.1768418 - 1) = 0.34$ rad (2) 4–∞h Dose rate:    $0.0815 \times 9.5\% \times 4 = 0.031$ rad/h Dose:    $0.004 \times \dfrac{9.5}{0.693} = 0.43$ rad (1) + (2):    0.77 rad <Total Body>

(1) 0–4h:

Dose rate:    $0.0815 \times 100\% \times \dfrac{4}{20^*} = 0.016$ rad/h

Dose:    $0.016 \int_0^4 e - \dfrac{0.693t}{T} dt = -0.326 \times \dfrac{0.5}{0.693} (0.0039109 - 1) = 0.01$ rad (2) 4–∞h Dose rate:    $0.0815 \times 4\% \times \dfrac{4}{20} = 0.001$ rad/h Dose:    $0.001 \times \dfrac{24}{0.693} = 0.02$ (1) + (2):    0.03 rad

EXAMPLE X

Description of $^{111}$In-BLMC

We have found that unfractioned $^{111}$In-BLM has 9 components (FIG. 10). $^{111}$In-BLMC has only one major component, the radiochemical purity of which is 99% (FIG. 1.2). Whether $^{111}$In-BLMC is one of the components of $^{111}$In-BLM mixture, or BLM that has undergone a structural change under the conditions (pH=2–3) when it chelates $^{111}$In is not known.

In the following experiments, $^{111}$In-BLMC solution, having pH of 2.5, was adjusted to pH 4.5 with 0.05 NaOH. Then, $^{111}$InCl$_3$ was added to this solution. The autoradiographs of TLC and 5% agarose gel electrophoresis are shown in FIG. 14.

Figure 14:
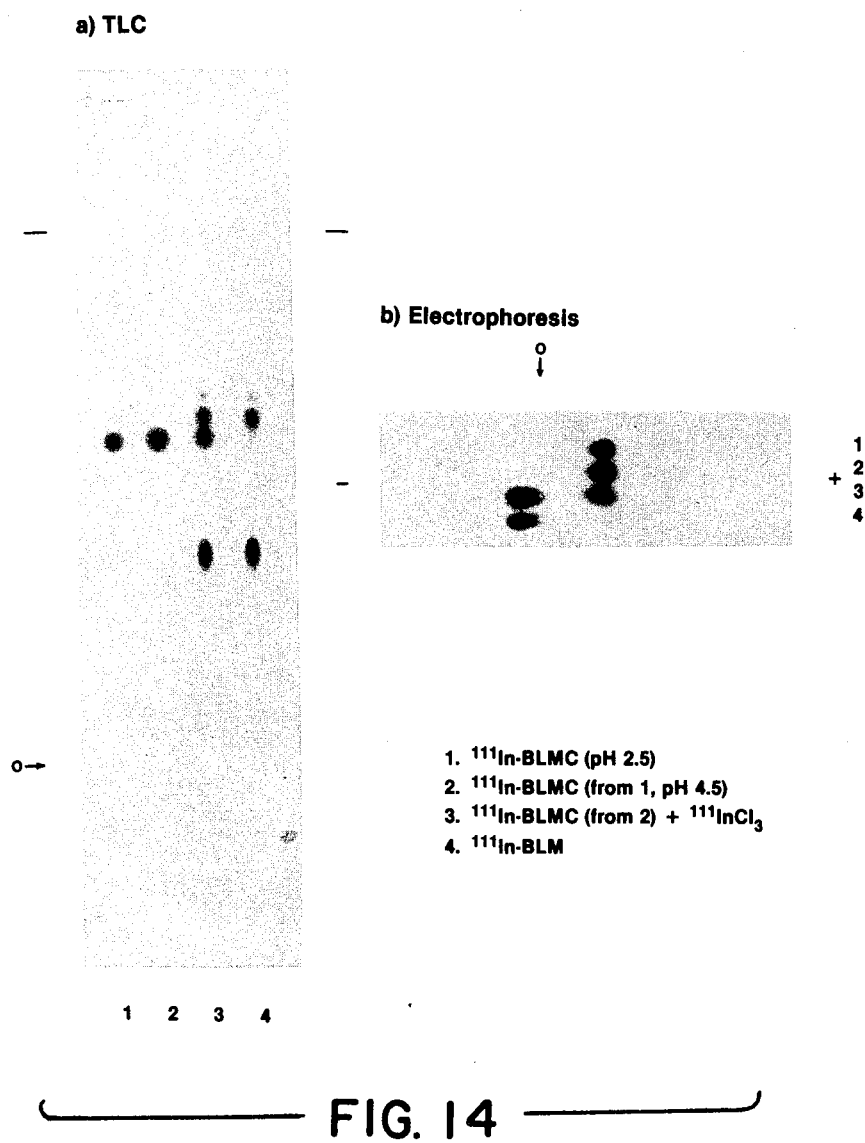
FIG. 14 is a graphic illustration describing $^{111}$In-BLMC.

FIG. 14 a, shows that the Rf of $^{111}$In-BLMC at pH 2.5 (lane 1) and of $^{111}$In-BLMC at pH 4.5 (lane 2) are the same, 0.65. The patterns of lane 3, $^{111}$In-BLMC (in pH 4.5) to which was added $^{111}$InCl$_3$ (in FIG. 14a, are similar to that of unfractionated $^{111}$In-BLM in lane 4 except for the largest spot of Rf=0.65. FIG. 14b shows the electrophoretic patterns of these solutions. A change in pH from 2.5 (lane 1) to 4.5 (lane 2) did not change the position of $^{111}$In-BLMC, which migrated toward the anode. Addition of $^{111}$InCl$_3$ to the solution at pH 4.5 (lane 3) resulted in additional components that migrated toward the cathode, a known property of $^{111}$In-BLM-A$_2$ and -B$_2$, which are shown in FIG. 14c, lane 4 and cf. FIG. 1c, lanes 3, 4, 5.

These results indicate that $^{111}$In-BLMC may be the same material as that appearing as spot No 4 in the TLC of unfractionated $^{111}$In-BLM (FIG. 14 cf, FIG. 10). This spot corresponds in position to a BLM component designated BLM-B$_3$ (Umezawa et al.: J. Antibiotics, Ser. A 19:2/82, 1966).

TABLE I

Distribution of $^{111}$In-BLMC, $^{111}$In-BLM-B$_2$ and $^{111}$In-BLM in Glioma-Bearing Mice[§] (at 24 hr)

| Radiopharmaceutical | % Dose/g Tissue (mean ± s.d.) | | | | | | |
|---|---|---|---|---|---|---|---|
| | Blood | Brain | Muscle | Heart | Lung | Liver | Spleen |
| $^{111}$In-BLMC (n = 2) | 0.018 ± 0.004* (0.057 ± 0.017)[§§] | 0.003 ± 0.001[++] | 0.019 ± 0.002** | 0.024 ± 0.001** | 0.041 ± 0.003** | 0.091 ± 0.007** | 0.100 ± 0.006* |
| $^{111}$In-BLM (n = 3) | 0.358 ± 0.097 (1.108 ± 0.48)[§§] | 0.054 ± 0.011[++] | 0.391 ± 0.048 | 0.450 ± 0.093[+] | 0.736 ± 0.105* | 1.358 ± 0.215** | 1.306 ± 0.193[+] |
| $^{111}$In-BLM-B$_2$ (n = 3) | 0.591 ± 0.120* | 0.065 ± 0.005**** | 0.441 ± 0.036*** | 0.598 ± | 1.004 ± | 2.642 ± | 1.358 ± |

TABLE I-continued

Distribution of $^{111}$In-BLMC, $^{111}$In-BLM-B$_2$ and $^{111}$In-BLM in Glioma-Bearing Mice$^\S$ (at 24 hr)

| | | | 0.076** | 0.094*** | 0.226*** | 0.263*** |
|---|---|---|---|---|---|---|
| Pancreas | Stomach | Femur | Skin | Kidney | Tumor | |
| 0.055 ± 0.019* | 0.045 ± 0.004*** | 0.118 ± 0.003** | 0.069 ± 0.009**** | 0.677 ± 0.045** | 0.232 ± 0.054**** | |
| 0.787 ± 0.209 | 0.735 ± 0.065**** | 2.055 ± 0.357++ | 1.150 ± 0.112++ | 11.008 ± 1.759* | 2.271 ± 0.122* | |
| 1.259 ± 0.737++ | 0.931 ± 0.158* | 2.480 ± 0.069**** | 1.661 ± 0.512* | 14.956 ± 1.361*** | 4.024 ± 0.573*** | |

*$p \leq 0.05$,
**$p \leq 0.01$,
***$p \leq 0.005$,
****$p \leq 0.001$,
+$0.05 < p \leq 0.1$, and
++$0.1 < p \leq 0.2$ in comparison of $^{111}$In-BLMC with $^{111}$In-BLM or $^{111}$In-BLM with $^{111}$In-BLM-B$_2$, or $^{111}$In-BLM-B$_2$ with $^{111}$In-BLMC (two-tailed t test)
$^\S$Tumor cell suspension transplanted ($1.5 \times 10^6$ cells)
$^{\S\S}p < 0.025$ in comparison of $^{111}$In-BLMC with $^{111}$In-BLM at 4 hr.

TABLE II

Activity Ratios of Tumor to Tissue in Glioma-Bearing Mice$^\S$ (at 24 hr.)

| | Tumor/Tissue (mean ± s.d.) | | | | | |
|---|---|---|---|---|---|---|
| Radiopharmaceutical | Blood | Brain | Muscle | Heart | Lung | Liver |
| $^{111}$In-BLMC (n = 2) | 13.07 ± 0.74* (4.98 ± 0.90)$^{\S\S}$ | 81.64 ± 0.61+ | 12.44 ± 1.34* | 9.70 ± 2.01++ | 5.61 ± 0.85++ | 1.96 ± 1.17 |
| $^{111}$In-BLM-B$_2$ (n = 3) | 7.14 ± 2.50 | 62.07 ± 11.15++ | 9.09 ± 0.73* | 6.87 ± 1.73++ | 4.05 ± 0.91 | 1.54 ± 0.30 |
| $^{111}$In-BLM (n = 3) | 6.64 ± 1.46* (1.54 ± 0.33)$^{\S\S}$ | 46.78 ± 9.49* | 6.29 ± 0.87** | 5.15 ± 0.77* | 3.35 ± 0.50* | 1.59 ± 0.20 |
| | Spleen | Pancreas | Stomach | Femur | Skin | Kidney |
| | 2.30 ± 0.42 | 4.35 ± 0.49 | 5.20 ± 0.85 | 1.98 ± 0.51 | 3.49 ± 1.19 | 0.34 ± 0.06++ |
| | 2.34 ± 0.55 | 4.01 ± 2.15 | 4.45 ± 1.19 | 1.63 ± 0.27+ | 2.51 ± 0.44 | 0.27 ± 0.02+ |
| | 1.90 ± 0.33 | 2.85 ± 0.78++ | 3.32 ± 0.20* | 1.21 ± 0.19* | 2.13 ± 0.22++ | 0.23 ± 0.04+ |

*$p \leq 0.05$,
**$p \leq 0.01$,
***$p \leq 0.005$,
****$p \leq 0.001$,
+$0.05 < p \leq 0.1$ and,
++$0.1 < p \leq 0.2$ in comparison of $^{111}$In-BLMC with $^{111}$In-BLM-B$_2$ or $^{111}$In-BLM-B$_2$ with $^{111}$In-BLM, or $^{111}$In-BLM with $^{111}$In-BLMC (two-tailed t test).
$^\S$Transplanted tumor cell suspension ($1.5 \times 10^6$ cells).
$^{\S\S}p < 0.005$ in comparison of $^{111}$In-BLMC with $^{111}$In-BLM (n = 3), at 4 hr.

TABLE III

Activity Ratios of Tumor to Tissue in Glioma Bearing Mice$^\S$ for $^{111}$In-BLMC

| | Tumor Tissue (mean ± s.d.) | | | | | |
|---|---|---|---|---|---|---|
| | Blood | Muscle | Brain | Liver | Lung | Stomach |
| 4 hr (n = 3) | 6.94 ± 1.0*** | 6.36 ± 1.78** | 33.31 ± 2.41* | 2.53 ± 0.25 | 5.21 ± 0.58+ | 3.32 ± 1.16 |
| 24 hr (n = 3) | 15.94 ± 1.96 | 12.32 ± 3.78 | 72.26 ± 12.76 | 2.43 ± 0.45 | 6.52 ± 0.70 | 4.94 ± 1.11 |

*$p \leq 0.05$,
**$p \leq 0.005$,
+$0.05 < p \leq 0.1$, and
++$0.1 < p \leq 0.2$ in comparison of 4 hr with 24 hr (two-tailed t test)
$^\S$Tumor tissue transplanted with trocn

TABLE IV

Tumor Size and Host Weight in Glioma-Bearing Mice Injected NaCl, BLM or $^{111}$In-BLMC (i.p.)

| Days after first Injection | Tumor Size, Mean ± S.D. ($d_1d_2d_3$, mm$^3$) | | | Host Weight, Mean ± S.D. (g) | | |
|---|---|---|---|---|---|---|
| | 0.9% NaCl (I) (n = 8) | BLM (II) (n = 5) | $^{111}$In-BLMC (III) (n = 4) | 0.9% NaCl (I) (n = 8) | BLM (II) (n = 5) | $^{111}$In-BLMC (III) (n = 4) |
| 0+ | 35 ± 14 | 31 ± 4 | 37 ± 9 | 24.3 ± 1.5 | 22.0 ± 0.9 | 22.4 ± 0.9 |
| 1 | 123 ± 15 | 62 ± 19** | 64 ± 32 | 23.1 ± 1.5 | 19.5 ± 0.6*** | 19.4 ± 1.1 |
| 2 | 152 ± 74 | 87 ± 20* | 48 ± 24* | 23.4 ± 1.2 | 19.5 ± 0.3*** | 18.3 ± 1.0 |
| 3 | 266 ± 144 | 131 ± 36* | 119 ± 8 | 23.2 ± 1.2 | 18.9 ± 0.6*** | 18.6 ± 0.7 |
| 4 | 571 ± 317 | 205 ± 54* | 96 ± 47* | 21.9 ± 1.2 | 18.4 ± 0.5*** | 18.3 ± 0.7 |
| 5 | 696 ± 374 | 351 ± 74 | 93 ± 45** | 22.3 ± 1.0 | 18.7 ± 0.3*** | 18.1 ± 0.4* |
| 6 | 1046 ± 441 | 500 ± 226* | 256 ± 90 | 20.8 ± 1.4 | 19.3 ± 0.6* | 18.2 ± 0.8* |
| 7 | 1559 ± 716 | 683 ± 199** | 264 ± 133** | 22.9 ± 1.3 | 19.7 ± 0.7*** | 19.2 ± 1.0 |
| 8 | 1663 ± 716$^\S$ | 763 ± 155 | 291 ± 135** | 22.4 ± 2.6 | 18.9 ± 0.7 | 18.5 ± 1.0 |
| 9 | 1885 ± 642 | 952 ± 381* | 304 ± 142* | 23.5 ± 1.9 | 18.7 ± 0.6* | 18.3 ± 1.2 |
| 10 | 2224 ± 845 | 1066 ± 383* | 314 ± 159** | 23.7 ± 1.4 | 19.2 ± 0.8*** | 18.8 ± 1.2 |
| 11 | 2796 ± 1072 | 1326 ± 339 | 373 ± 186** | 23.3 ± 0.9 | 19.7 ± 1.1 | 18.7 ± 1.8 |
| 12 | 3455 ± 1286 | 1507 ± 356* | 456 ± 269*** | 22.8 ± 1.1 | 18.7 ± 0.9*** | 18.8 ± 1.8 |
| 13 | 3595 ± 1870 | 1697 ± 390 | 492 ± 266*** | 22.7 ± 2.2 | 19.7 ± 1.0* | 19.2 ± 2.0 |
| 14 | 3587 ± 1878 | 1671 ± 443 | 516 ± 304** | 23.2 ± 2.5 | 20.9 ± 1.0 | 19.4 ± 2.7 |

TABLE IV-continued

Tumor Size and Host Weight in Glioma-Bearing Mice Injected NaCl, BLM or $^{111}$In-BLMC (i.p.)

| Days after first Injection | Tumor Size, Mean ± S.D. ($d_1d_2d_3$, mm$^3$) | | | Host Weight, Mean ± S.D. (g) | | |
|---|---|---|---|---|---|---|
| | 0.9% NaCl (I) (n = 8) | BLM (II) (n = 5) | $^{111}$In-BLMC (III) (n = 4) | 0.9% NaCl (I) (n = 8) | BLM (II) (n = 5) | $^{111}$In-BLMC (III) (n = 4) |
| 15 | 4404 ± 2942 | 1965 ± 697 | 518 ± 380** | 23.5 ± 2.1 | 21.1 ± 0.9* | 20.1 ± 2.5 |
| 16+ | 4833 ± 3034 | 1975 ± 756 | 563 ± 374** | 23.9 ± 1.8 | 21.9 ± 1.0 | 21.4 ± 2.5 |

*p ≦ 0.05,
**p ≦ 0.01,
***p ≦ 0.001 for comparison of 0.9% NaCl group with BLM group, and BLM group with $^{111}$In-BLMC group (two-tailed t test).
§n = 4 after this day.
+tumor age 6–22 days

TABLE V

Tumor Size and Host Weight in Glioma-Bearing Mice Injected NaCl, BLM or $^{111}$In-BLMC (i.t.)

| Days after Therapy | Tumor Size, Mean ± S.D. ($d_1d_2d_3$, mm$^3$) | | | Host Weight, Mean ± S.D. (g) | | |
|---|---|---|---|---|---|---|
| | 0.9% NaCl (IV) (n = 3) | BLM (V) (n = 3) | $^{111}$In-BLMC (VI) (n = 3) | 0.9% NaCl (IV) (n = 3) | BLM (V) (n = 3) | $^{111}$In-BLMC (VI) (n = 3) |
| 0+ | 2266 ± 883 | 1643 ± 330 | 1545 ± 308 | 21.9 ± 3.3 | 23.4 ± 2.5 | 22.2 ± 1.6 |
| 1 | 2871 ± 1125 | 1962 ± 583 | 1308 ± 162 | 23.2 ± 3.9 | 23.0 ± 1.5 | 21.4 ± 2.3 |
| 2 | 2957 ± 936 | 2052 ± 209 | 1078 ± 282** | 23.4 ± 4.4 | 22.6 ± 1.3 | 21.2 ± 2.4 |
| 3 | 3656 ± 1194 | 2095 ± 565 | 695 ± 70* | 23.1 ± 4.0 | 23.3 ± 0.4 | 21.4 ± 2.8 |
| 4 | 4043 ± 1328 | 2818 ± 249 | 766 ± 142** | 22.1 ± 3.6 | 22.2 ± 1.5 | 20.4 ± 2.2 |
| 5 | 4200 ± 1246 | 2659 ± 792 | 828 ± 314** | 21.8 ± 3.6 | 22.7 ± 0.9 | 21.1 ± 2.4 |
| 6 | 4865 ± 1177 | 2745 ± 690 | 792 ± 275** | 21.6 ± 4.1 | 22.8 ± 1.2 | 20.9 ± 2.3 |
| 7 | 5021 ± 1630 | 2492 ± 573 | 887 ± 551* | 22.8 ± 4.5 | 22.9 ± 1.3 | 21.2 ± 1.9 |
| 8 | 5451 ± 1692 | 2582 ± 462* | 1059 ± 637* | 23.5 ± 5.4 | 22.2 ± 0.8 | 21.2 ± 1.9 |
| 9+ | 6023 ± 1701 | 2683 ± 581* | 1059 ± 647* | 23.9 ± 6.8 | 23.4 ± 1.7 | 21.9 ± 1.7 |

*p ≦ 0.05,
**p ≦ 0.01,
***p ≦ 0.001 for comparison of 0.9% NaCl group with BLM group, and BLM group with $^{111}$In-BLMC group (two-tailed t test)
+tumor age 13–22 days.

TABLE VI

Tumor Size in Glioma-Bearing Mice Injected 0.9% NaCl or Cold In-BLMC (i.p.)

| Days after First Injection | Tumor Size, Mean ± S.D. ($d_1d_2d_3$, mm$^3$) | | Host Weight, Mean ± S.D. (g) | |
|---|---|---|---|---|
| | 0.9% NaCl (VII) (n = 5) | In-BLMC (VIII) (n = 5) | 0.9% NaCl (VII) (n = 5) | In-BLMC (VIII) (n = 5) |
| 0+ | 140 ± 19 | 129 ± 13 | 22.1 ± 1.1 | 22.1 ± 1.9 |
| 1 | 210 ± 31 | 175 ± 33 | 21.8 ± 1.2 | 20.5 ± 1.0 |
| 2 | 390 ± 113 | 277 ± 74 | 21.6 ± 1.1 | 19.4 ± 0.7** |
| 3 | 449 ± 99 | 375 ± 41 | 21.3 ± 1.2 | 19.0 ± 1.0** |
| 4 | 686 ± 88 | 405 ± 17** | 21.2 ± 1.7 | 19.2 ± 0.7* |
| 5 | 1085 ± 341 | 631 ± 298* | 20.6 ± 1.4 | 19.6 ± 1.0 |
| 6 | 1967 ± 540 | 785 ± 265** | 19.6 ± 1.8 | 18.7 ± 1.1 |
| 7 | 2505 ± 445 (4)§ | 1089 ± 293** | 20.3 ± 1.6 | 18.9 ± 1.3 |
| 8 | 2897 ± 287 | 1129 ± 308*** | 20.1 ± 2.0 | 18.8 ± 1.2 |
| 9 | 2838 ± 679 (3) | 1787 ± 743 | 19.5 ± 1.1 | 18.8 ± 1.1 |
| 10 | 2935 ± 148 | 1635 ± 631* | 19.3 ± 1.7 | 18.4 ± 1.6 |
| 11 | 3885 ± 727 | 1929 ± 587** | 16.2 ± 1.8 | 17.6 ± 1.5 |
| 12 | 4766 ± 1013 (2) | 2199 ± 670** | 18.4 ± 0.4 | 18.4 ± 1.4 |
| 13 | 4910 ± 500 | 2614 ± 640** | 19.4 ± 0.7 | 18.7 ± 1.3 |
| 14 | 5601 ± 199 | 3155 ± 1115* | 20.4 ± 0.0 | 19.2 ± 0.9 |
| 15 | 7153 ± 712 | 3706 ± 1287* | 19.7 ± 0.1 | 18.5 ± 1.4 |
| 16+ | 7895 (1) | 4027 ± 1266* | 16.7 | 16.4 ± 1.4 |

*p ≦ 0.05,
**p ≦ 0.01,
***p ≦ 0.001 for comparison of 0.9% NaCl group with nonradioactive In-BLMC group (two-tailed t test).
§( ) number of mice.
+tumor age 6–22 days.

TABLE VII

Tumor Size in Glioma-Bearing Mice Injected 0.9% NaCl or Cold InCl$_3$ (i.t.)

| Days after Therapy | Tumor Size, Mean ± S.D. ($d_1d_2d_3$, mm$^3$) | | Host Weight, Mean ± S.D. (g) | |
|---|---|---|---|---|
| | 0.9% NaCl (IX) (n = 2) | InCl$_3$ (X) (n = 3) | 0.9% NaCl (IX) (n = 2) | InCl$_3$ (X) (n = 3) |
| 0+ | 1872 ± 3 | 1238 ± 711 | 21.2 ± 2.3 | 20.3 ± 2.5 |
| 1 | 2524 ± 5 | 1741 ± 701 | 20.5 ± 2.6 | 20.4 ± 1.6 |
| 2 | 2606 ± 121 | 1998 ± 559 | 20.6 ± 2.5 | 20.0 ± 1.6 |
| 3 | 2956 ± 173 | 2496 ± 395 | 21.3 ± 2.8 | 20.0 ± 1.5 |
| 4 | 3465 ± 446 | 2720 ± 503 | 20.5 ± 3.5 | 20.0 ± 1.5 |

TABLE VII-continued

Tumor Size in Glioma-Bearing Mice Injected 0.9% NaCl or Cold InCl$_3$ (i.t.)

| Days after Therapy | Tumor Size, Mean ± S.D. (d$_1$d$_2$d$_3$, mm$^3$) | | Host Weight, Mean ± S.D. (g) | |
| --- | --- | --- | --- | --- |
| | 0.9% NaCl (IX) (n = 2) | InCl$_3$ (X) (n = 3) | 0.9% NaCl (IX) (n = 2) | InCl$_3$ (X) (n = 3) |
| 5 | 3790 ± 505 | 3333 ± 276 | 19.6 ± 3.0 | 19.9 ± 1.6 |
| 6 | 4317 ± 307 | 3882 ± 501 | 17.7 ± 3.1 | 17.9 ± 1.9 |
| 7 | 5944 ± 144 | 5015 ± 936 | 18.6 ± 4.0 | 18.8 ± 2.9 |
| 8 | 6739 ± 313 | 5234 ± 1146 | 18.9 ± 4.8 | 19.1 ± 2.4 |
| 9+ | 6886 ± 105 | 5988 ± 492 | 19.0 ± 4.7 | 20.3 ± 3.8 |

+tumor age 13–22 days.

What is claimed is:

1. Substantially radiochemically pure ($^{111}$I-BLMC) complex lacking binding capacity for serum transferrin.

2. In a diagnostic method for gamma imaging of tumors in mammals of the type wherein a gamma-emitting radionuclide is administered to the host as a tumor-imaging agent and the host is scanned with a gamma counter to visualize the tumor, the improvement comprising administering $^{111}$In-BLMC according to claim 1 as the tumor-imaging agent.

3. In a method for treating tumors in mammals of the type wherein a radiopharmaceutical is administered to a host in therapeutic amounts to control the growth of the tumor, the improvement comprising administering $^{111}$In-BLMC according to claim 1 as the radiopharmaceutical.

4. The method of claim 2, wherein the tumor is a glioma.

5. The method of claim 3, wherein the tumor is a glioma.

6. The method of claim 2, wherein the mammal is a human.

7. The method of claim 3, wherein the mammal is a human.

8. A method for the preparation of an $^{111}$In-BLMC complex of bleomycin and $^{111}$Indium (III) lacking capacity for binding to serum transferrin, comprising reacting a bleomycin mixture derived from a culture broth of Streptomyces verticillus with $^{111}$InCl$_3$ at a pH of from about 1.5 to about 3.0.

9. The method of claim 8, wherein $^{111}$InCl$_3$ is in the form of an acid solution having a pH of from about 1 to about 3.

10. The method of claim 8, wherein a diluent is employed in admixture with one of the reactants used to adjust the pH thereof.

11. The method of claim 8, wherein the pH of the reaction is from about 2 to about 3.

12. The method of claim 2, wherein the tumor-imaging agent comprises a solution consisting essentially of substantially radiochemically pure $^{111}$In-BLMC prepared by reacting an acidic solution of $^{111}$InCl$_3$ and a bleomycin mixture at a reaction pH of from about 1.5 to about 3.

13. The method of claim 12, wherein the bleomycin is in solid form.

14. The method of claim 8, wherein bleomycin is in solid form.

15. The method of claim 12, wherein bleomycin and $^{111}$InCl$_3$ are reacted in proportions of about 1.0 mg. solid bleomycin to about 25 μl to 200 μl of $^{111}$InCl$_3$ at a concentration of about 2 mCi/ml.

16. The method of claim 12, wherein the proportion of $^{111}$InCl$_3$ is from about 50 μl to about 100 μl.

17. The method of claim 12, wherein a pharmaceutically-acceptable diluent is premixed with one of the reactants used to adjust the pH of the reaction solution.

18. The method of claim 12, wherein $^{111}$InCl$_3$ and bleomycin are reacted at a pH of from about 2 to about 3.

19. The method of claim 17, wherein the diluent is normal saline.

20. The method of claim 12, wherein unreacted bleomycin and/or unreacted $^{111}$In(III) is removed from the solution before it is administered.

21. The method of claim 3, wherein the radio-pharmaceutical administered to the host comprises a solution consisting essentially of substantially radiochemically pure $^{111}$In-BLMC prepared by reacting an acidic solution of $^{111}$InCl$_3$ and a bleomycin mixture at a pH of from about 1.5 to about 3.

22. The $^{111}$In-BLMC of claim 1 having an Rf of 0.65 (10% aqueous ammonium acetate/methanol 1:1 v/v as eluant).

23. $^{111}$In-BLMC prepared by the method of claim 8.

* * * * *